(12) United States Patent
Schlaepfer et al.

(10) Patent No.: US 8,197,519 B2
(45) Date of Patent: Jun. 12, 2012

(54) BONE SUPPORT APPARATUS

(75) Inventors: Fridolin Schlaepfer, Hoelstein (CH);
Renzo De Franceschi, Gretzenbach (CH)

(73) Assignee: Synthes USA, LLC, West Chester, PA (US)

( * ) Notice: Subject to any disclaimer, the term of this patent is extended or adjusted under 35 U.S.C. 154(b) by 493 days.

(21) Appl. No.: 12/067,157

(22) PCT Filed: Sep. 22, 2006

(86) PCT No.: PCT/US2006/037120
§ 371 (c)(1),
(2), (4) Date: Sep. 8, 2008

(87) PCT Pub. No.: WO2007/038350
PCT Pub. Date: Apr. 5, 2007

(65) Prior Publication Data
US 2009/0149887 A1    Jun. 11, 2009

(51) Int. Cl.
*A61B 17/70* (2006.01)
(52) U.S. Cl. ........................................ 606/278
(58) Field of Classification Search ............... 606/60, 606/264–270, 300–308
See application file for complete search history.

(56) References Cited

U.S. PATENT DOCUMENTS

| | | | | |
|---|---|---|---|---|
| 5,586,984 A * | 12/1996 | Errico et al. | | 606/264 |
| 6,565,565 B1 * | 5/2003 | Yuan et al. | | 606/272 |
| 6,755,829 B1 * | 6/2004 | Bono et al. | | 606/308 |
| 2004/0039384 A1 * | 2/2004 | Boehm et al. | | 606/61 |
| 2005/0177154 A1 | 8/2005 | Moumene et al. | | |
| 2006/0247636 A1 * | 11/2006 | Yuan et al. | | 606/61 |

FOREIGN PATENT DOCUMENTS

WO     WO 2004/089245     10/2004

OTHER PUBLICATIONS

International Search Report, completed Jan. 19, 2007 for International Application No. PCT/US2006/037120, filed Sep. 22, 2006.

* cited by examiner

*Primary Examiner* — Eduardo C Robert
*Assistant Examiner* — Stuart S Bray
(74) *Attorney, Agent, or Firm* — Woodcock Washburn LLP

(57) ABSTRACT

An apparatus for connecting a bone anchor to a support rod includes a connector body and a cap. The connector body has a channel to receive and locate the support rod relative to the bone anchor. The cap is moveable longitudinally into a partially installed position in the channel, and snaps into non-threaded engagement with the connector body by rotating from the partially installed position to an installed position without moving axially relative to the connector body. In some embodiments, a sleeve fits over a socket portion of the connector body in a temporary position in which the sleeve permits insertion of the bone anchor into the socket. The sleeve engages the connector body so as to be restrained from axial and rotational movement relative to the connector body when in the temporary position. Tools are provided for installing the connector body, sleeve, cap, and support rod.

26 Claims, 22 Drawing Sheets

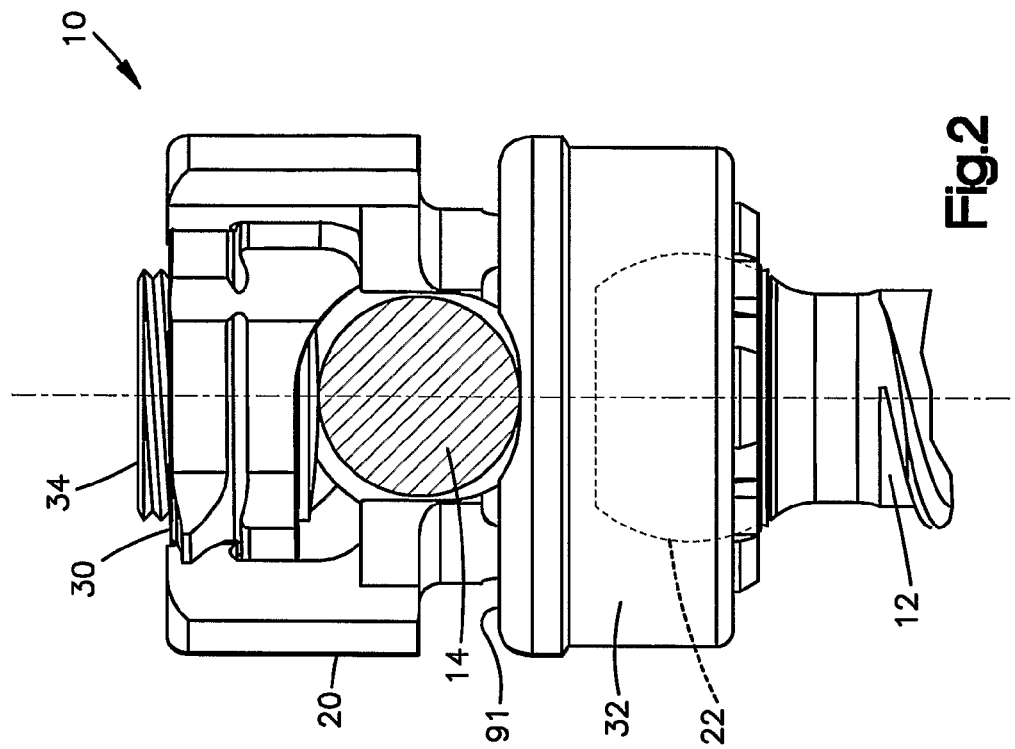
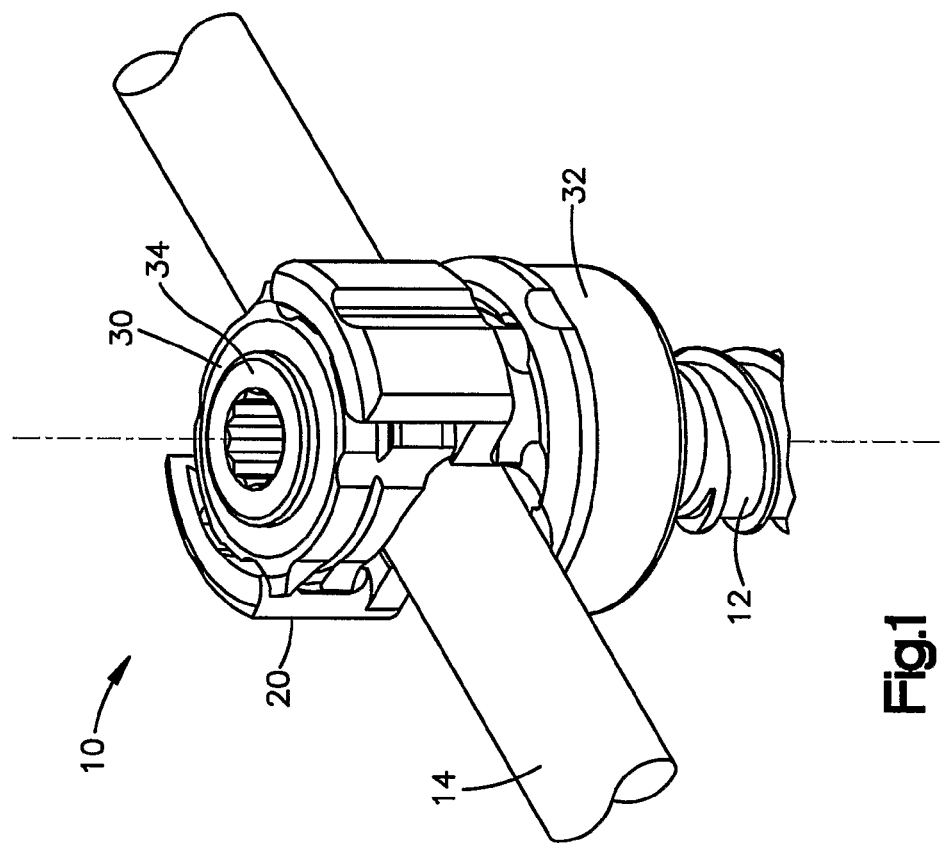

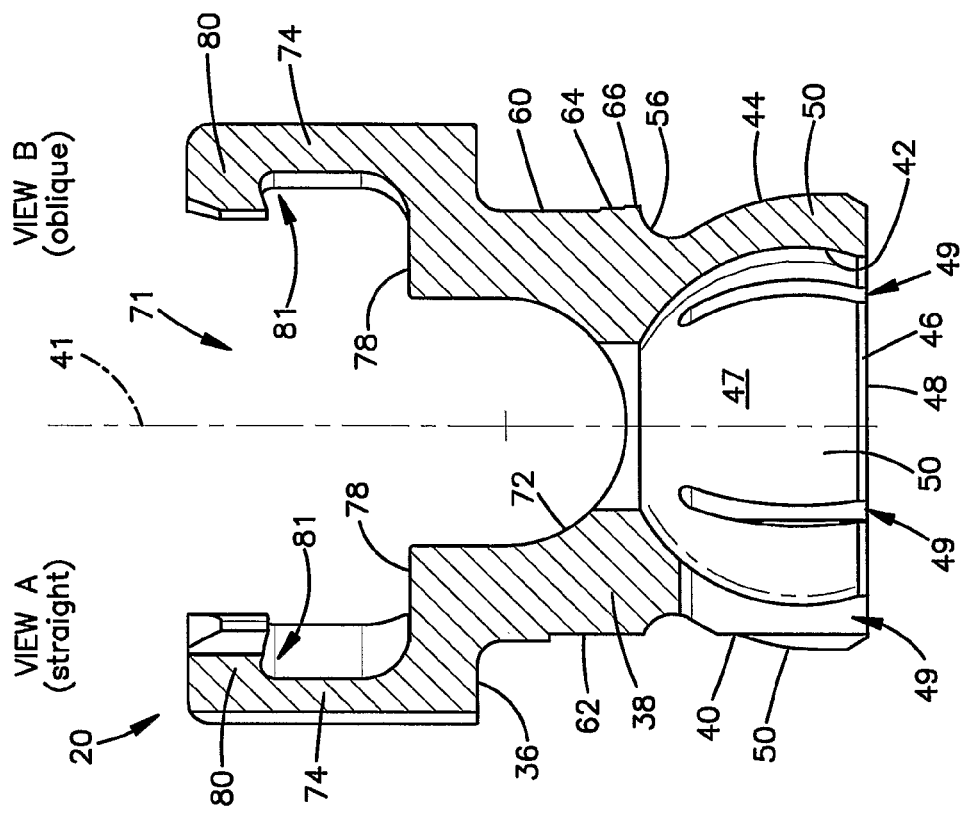
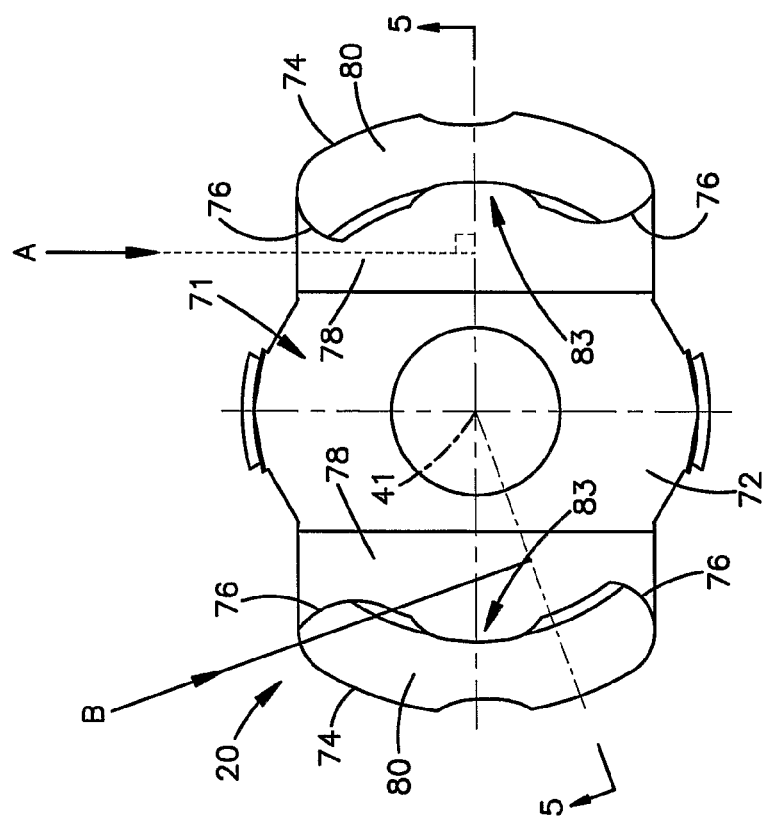

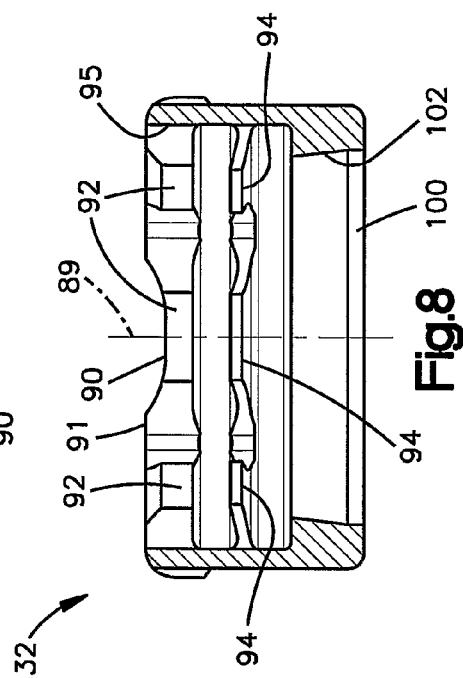
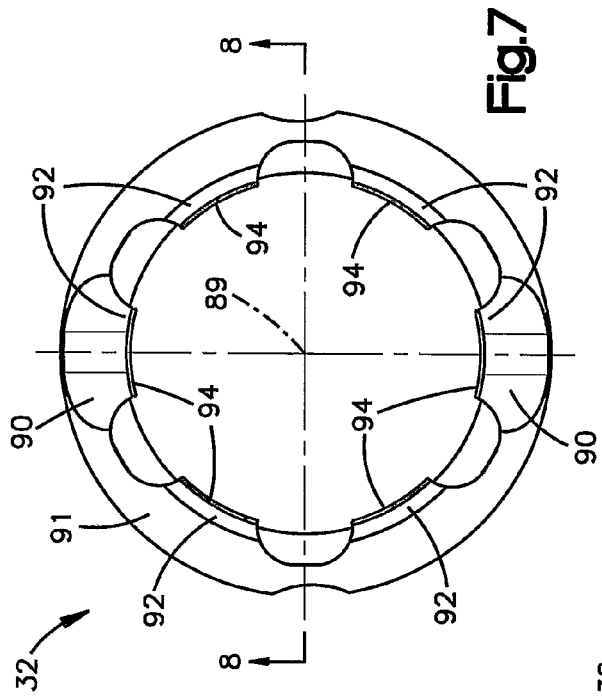
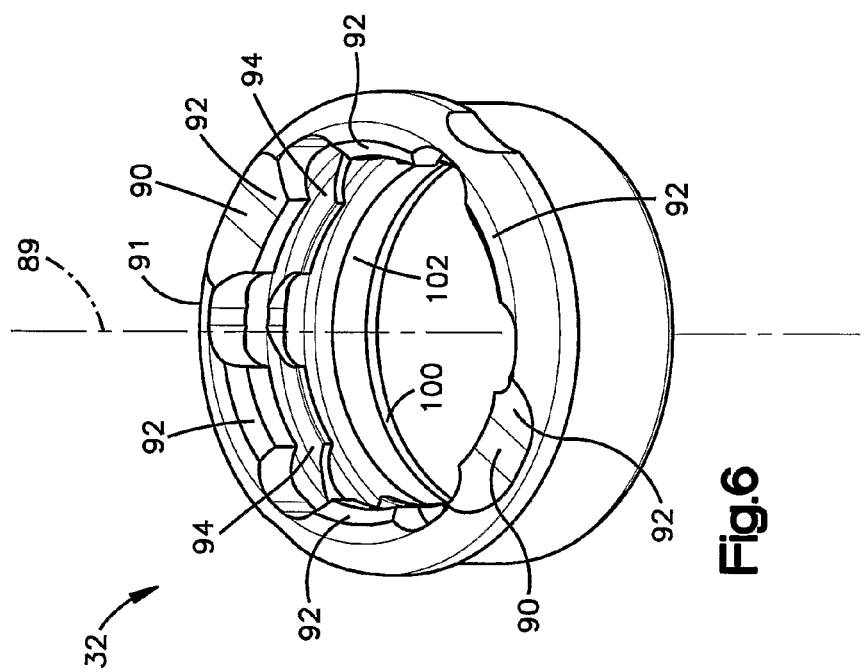

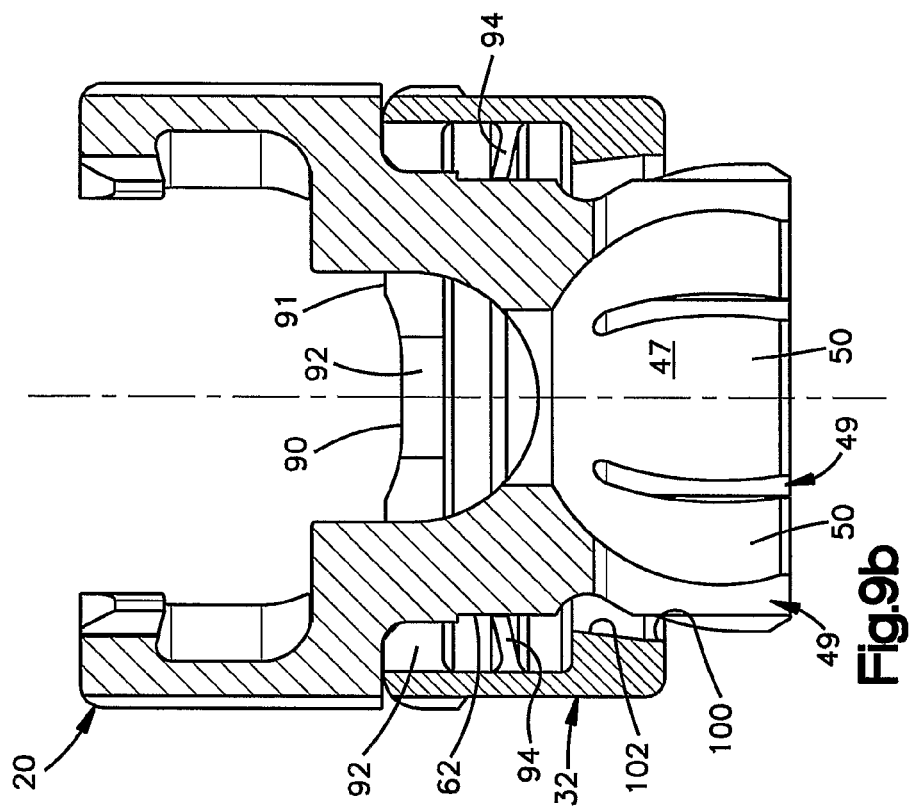
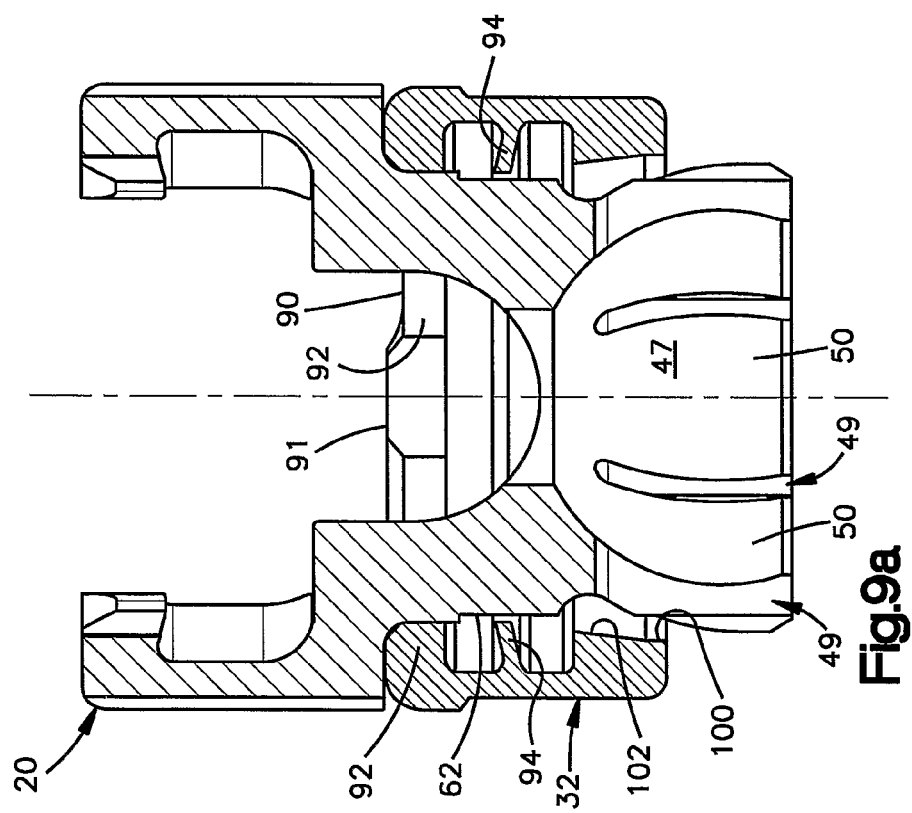

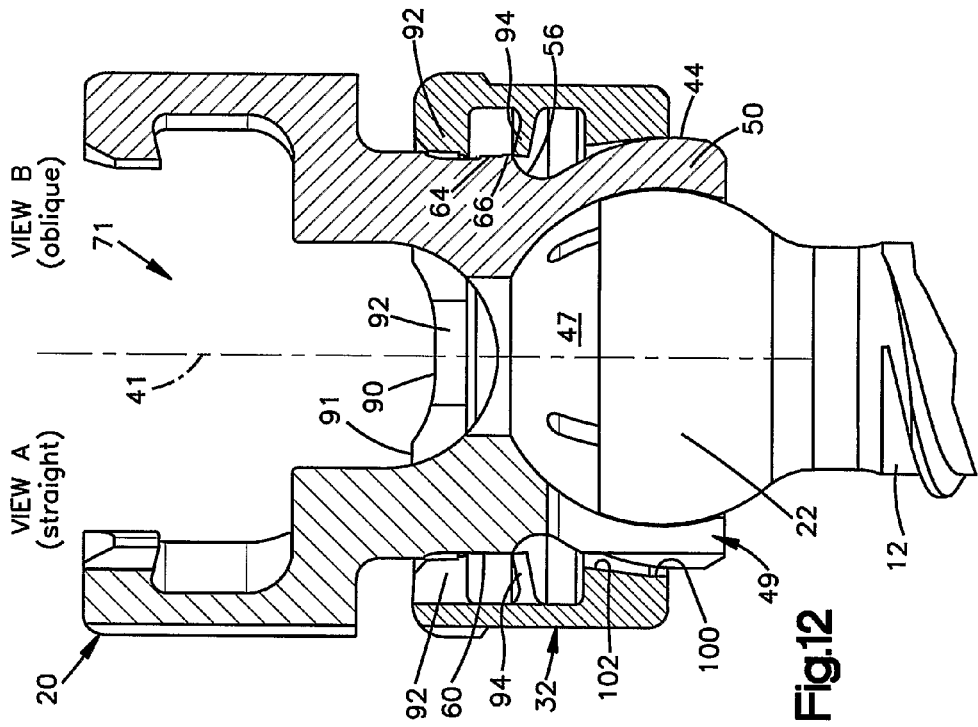
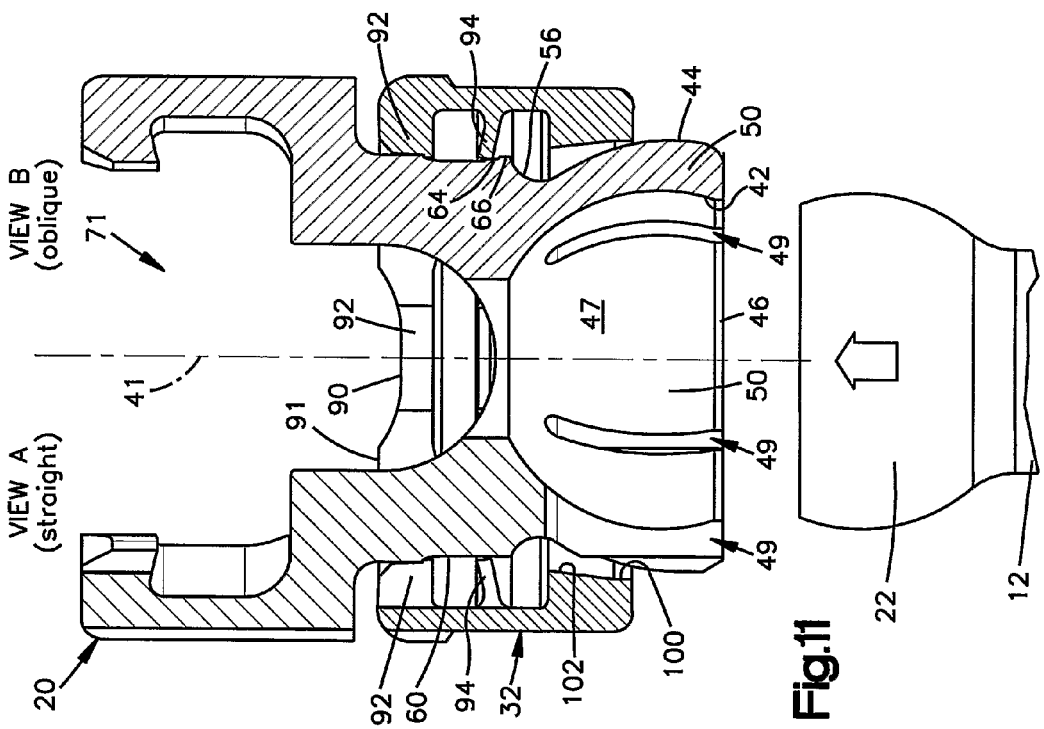
Fig.11
Fig.12

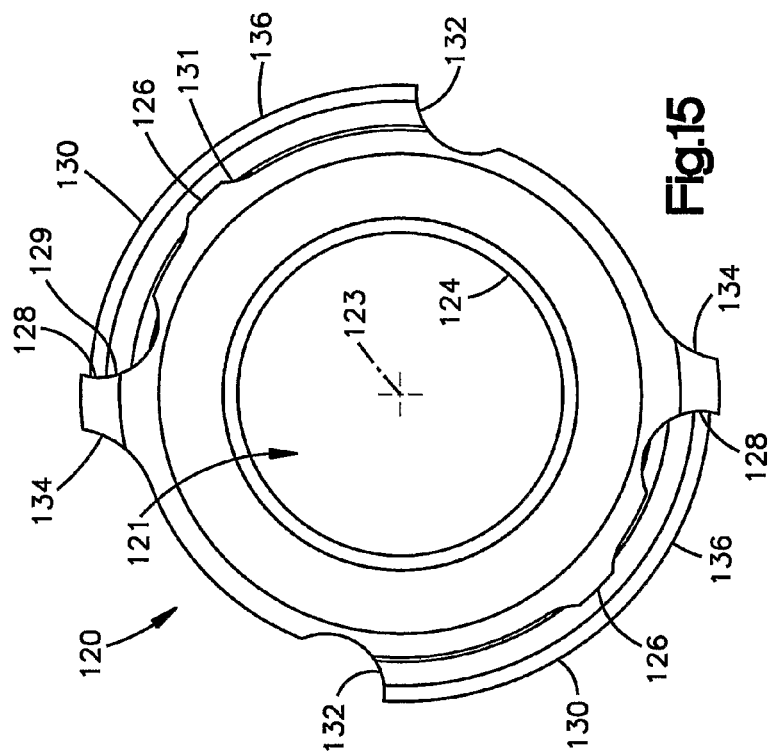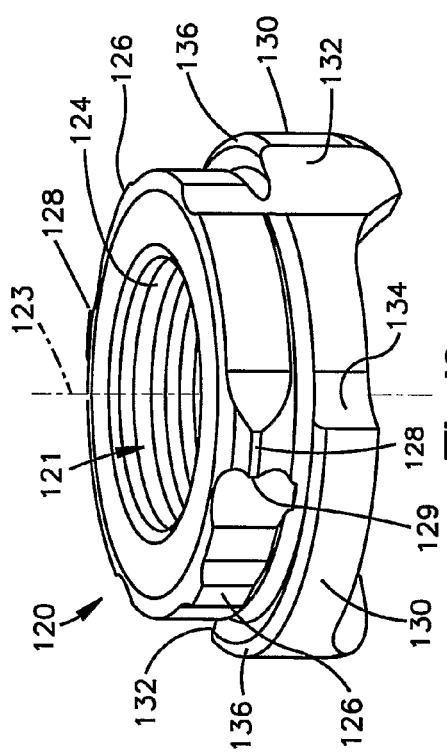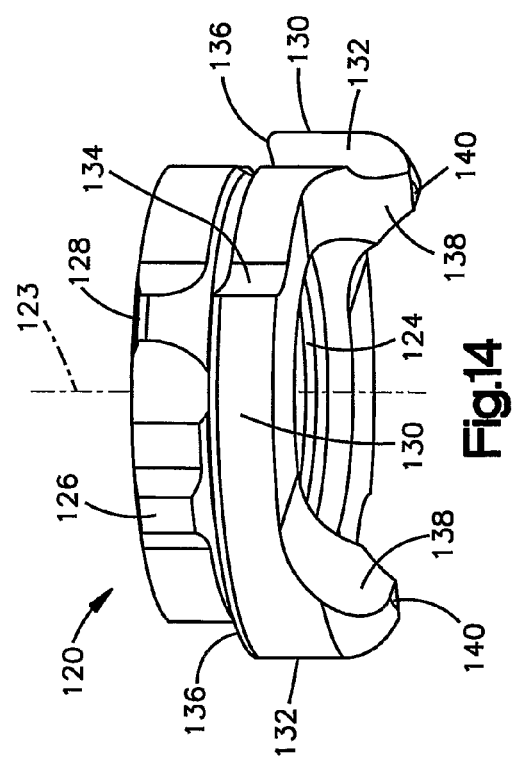

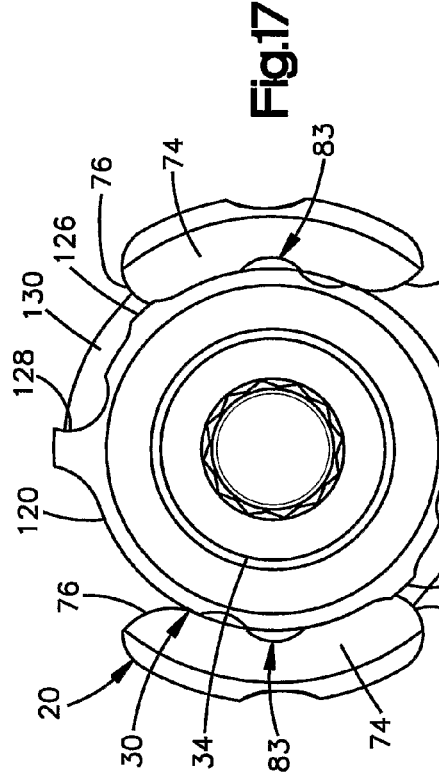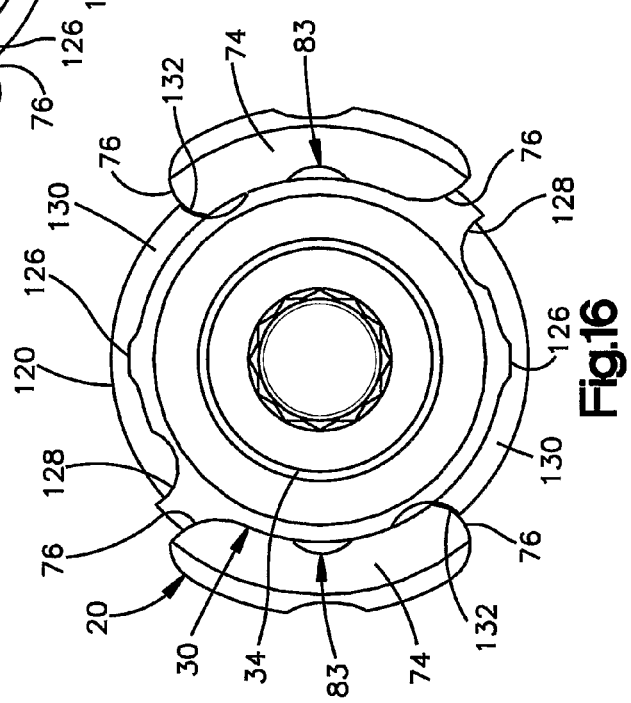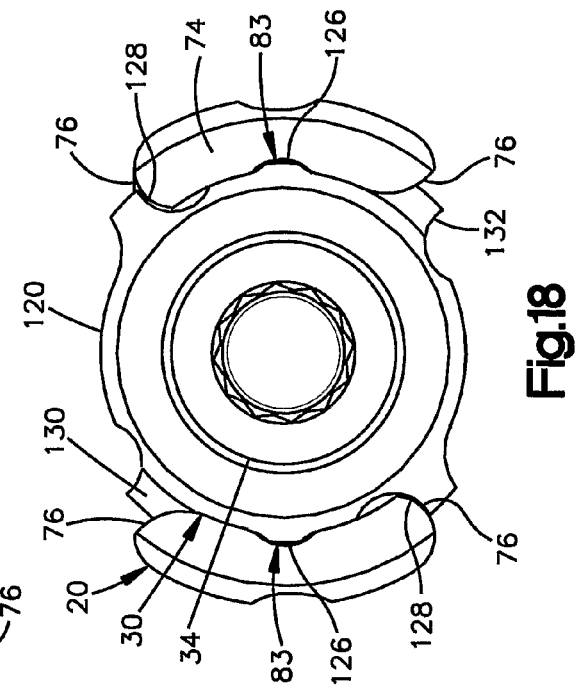

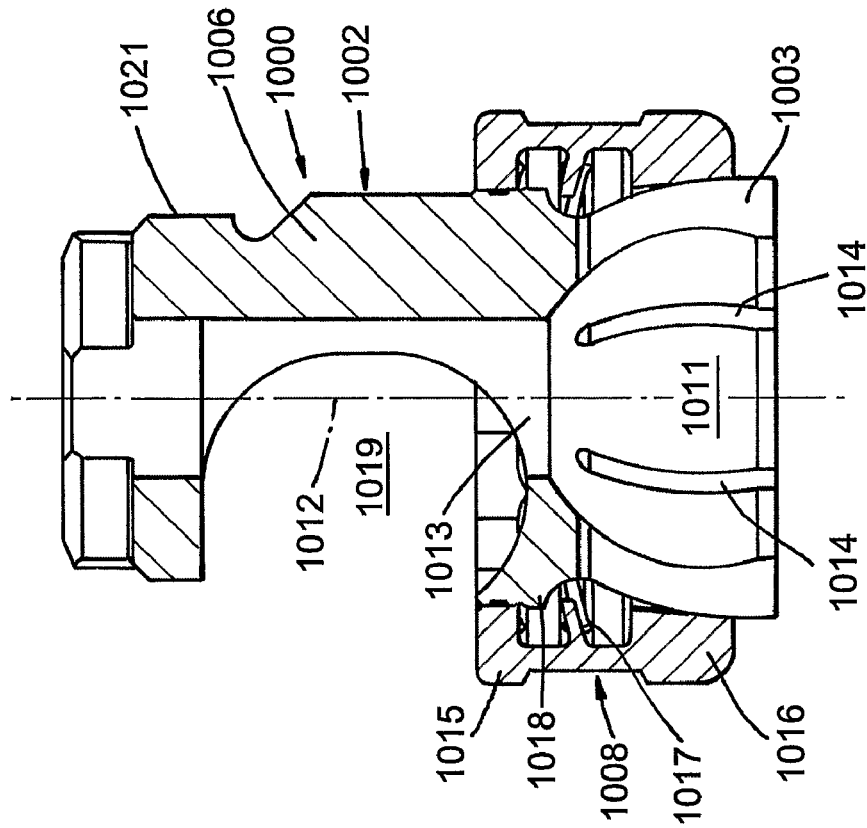
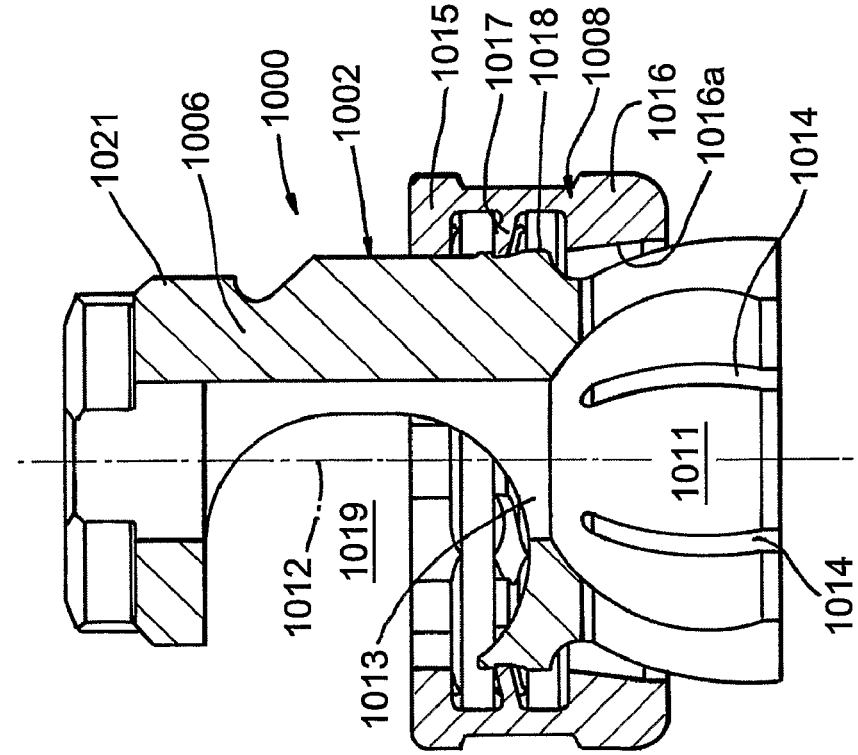

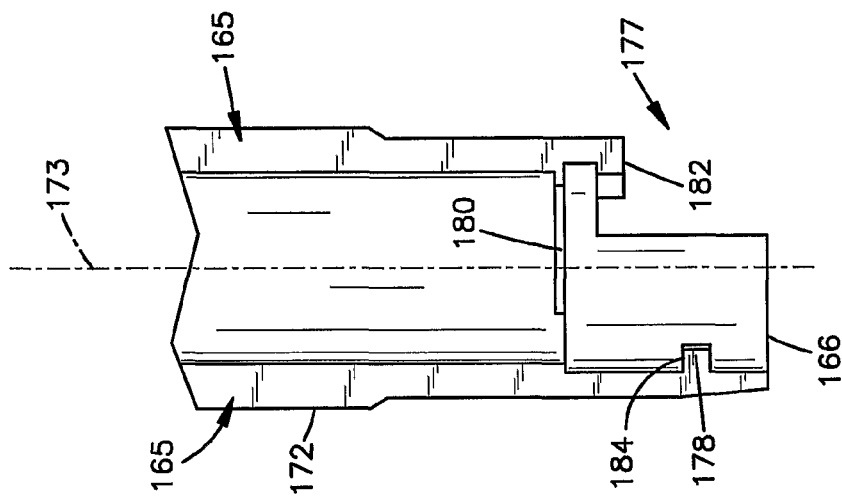
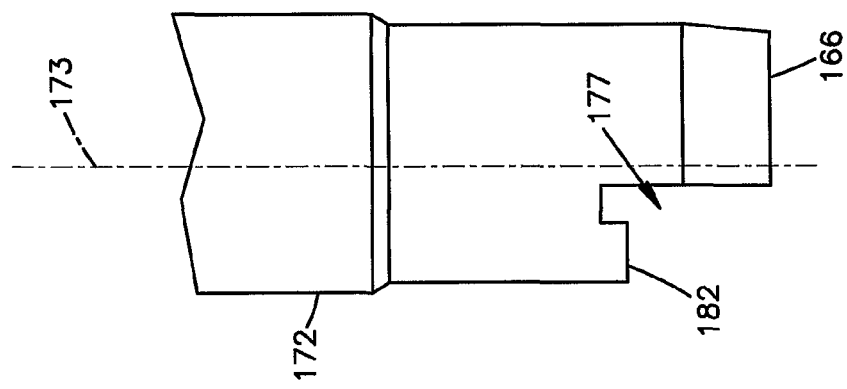
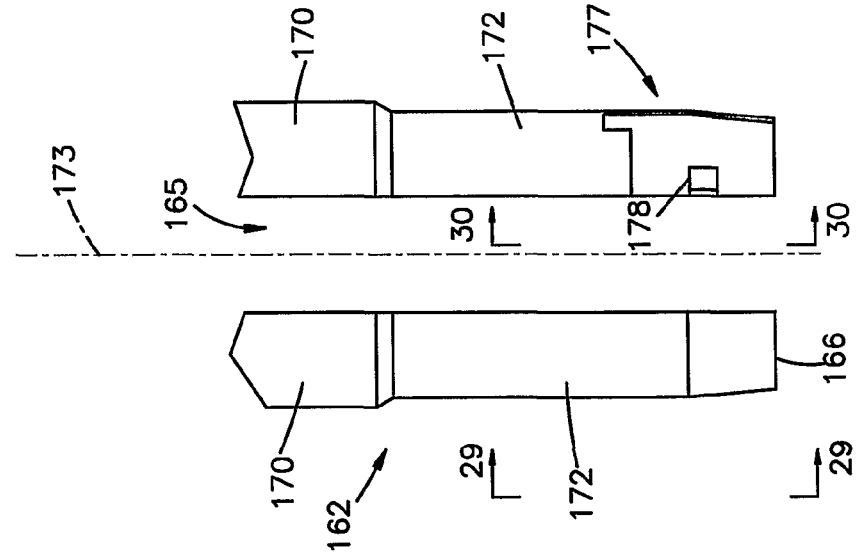

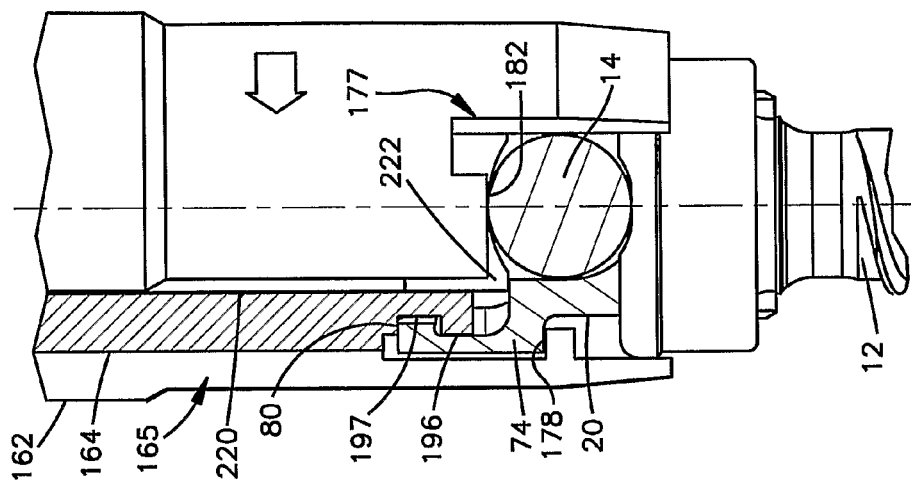
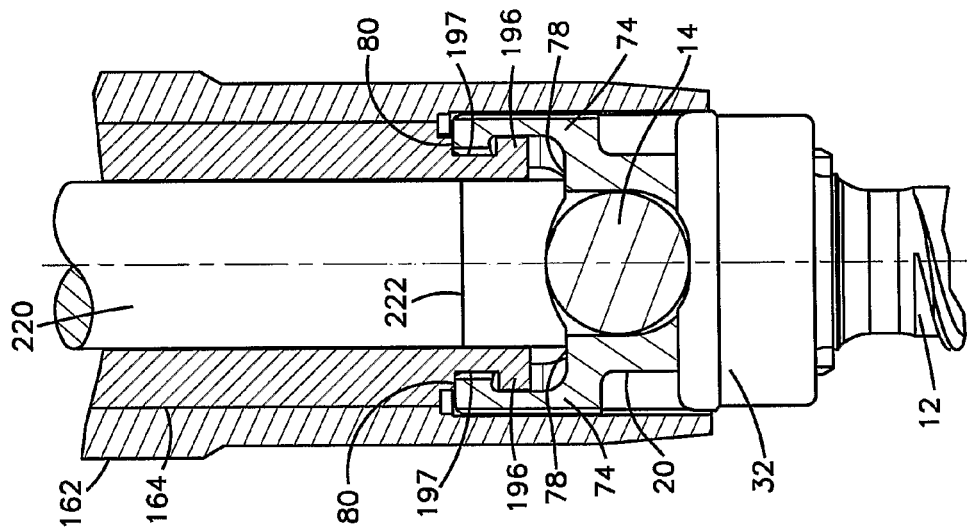
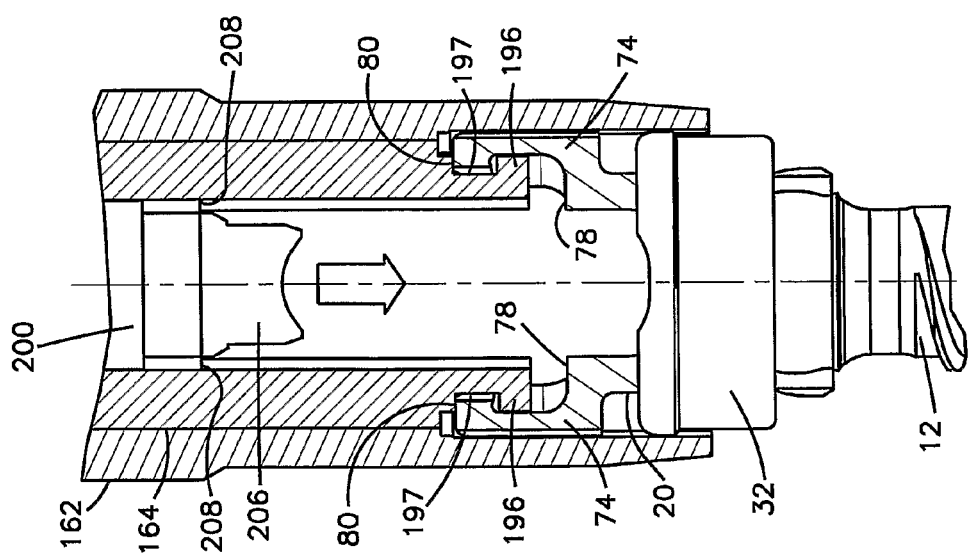

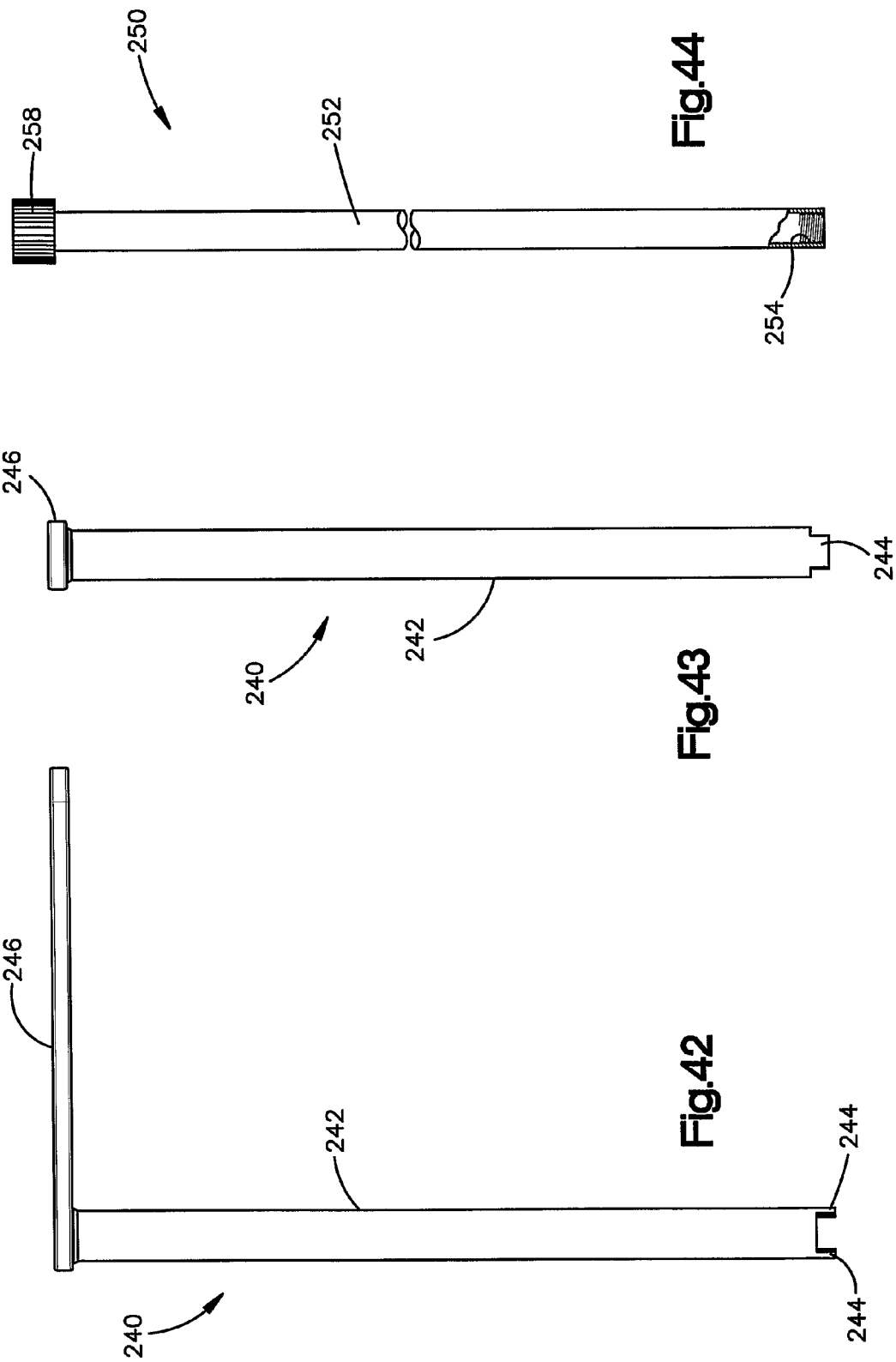

BONE SUPPORT APPARATUS

TECHNICAL FIELD

The claimed invention relates to a device for connecting a bone support member to a bone anchor, and more specifically a bone screw or hook to a support rod.

BACKGROUND

Many methods of treating spinal disorders are known in the art. One known method involves anchoring a screw or a hook to the vertebrae, and fixing the screws or hooks along a spinal rod to position or immobilize the vertebrae with respect to one another. The screws or hooks commonly have heads with channels in which the spinal rod is inserted and subsequently clamped by a set screw or fastener or locking cap. This method may commonly involve multiple screws or hooks, as well as multiple spinal rods. With this method, the spinal rod(s) may be shaped to maintain the vertebrae in such an orientation as to correct the spinal disorder at hand (e.g. to straighten a spine having abnormal curvature). Additionally or alternatively, the screws or hooks my be spaced along the rod(s) to compress or distract adjacent vertebrae.

Surgeons have often encountered considerably difficulty with this method because of trouble aligning the spinal rod(s) with the channels in the heads of the screws or hooks. For example, the heads of the screws or hooks are often out of alignment with one another because of the curvature of the spine or the size and shape of each vertebrae. To facilitate easier insertion of the spinal rods into the channels, and to provide additional flexibility in the positioning of the spinal rods and the screws and hooks, connectors have been developed (which include the support rod channel) which initially pivots with respect to the anchor member (e.g., screw or hook). One example of such a screw assembly is disclosed in U.S. Pat. No. 5,586,984 to Errico et al., which is incorporated herein by reference.

The process of positioning and setting known bone anchors may be tedious and relatively time-consuming, typically requiring more than one surgical tool to clamp the spinal rod and anchor member in desired positions. Even with a high degree of skill and care, the process of positioning a known bone anchor assembly and then manipulating the connector to clamp or re-clamp the spinal rod and bone anchor in place can tale more time than desired during a surgical procedure or even resulting in the rod, anchor member, or both moving out of position before clamping is completed. Furthermore, the preassembled connectors and bone anchors require a large inventory of assemblies to accommodate the various size rods and bone anchors necessary to fit the variety of patient sizes.

Therefore, a need still exists for bone anchors including polyaxial bone anchors that provide an improved mechanism for clamping the spinal rod and anchor member in their desired positions, and can reduce the inventory requirements at the medical facility.

SUMMARY

An apparatus for connecting a bone anchor to a support rod comprises a connector body and a cap. The connector body has a channel, preferably a U-shaped channel, that receives and locates the support rod relative to the bone anchor. The cap secures the support rod in the channel. The cap is movable into a partially installed position in the channel, preferably by moving the cap axially down along the longitudinal axis, and then into attachment with the connector body by rotating from the partially installed position to an installed position without moving axially along the longitudinal axis relative to the connector body. The cap preferably comprises a ring and a set screw. The ring preferably attaches to the connector body but preferably does not lock or clamp the support rod or the bone anchor. More specifically, the ring and set screw assembly moves axially down the longitudinal axis into a partially installed position and the ring alone, or ring and set screw assembly, are preferably rotated about 90° to an installed position where the ring and set screw are attached to the connector body. Preferably at this point, the support rod is retained within the connector body but movable with respect to the connector body. Also, preferably at this point, the bone anchor, if a polyaxial bone anchor assembly, can rotate and angulate within the connector body. Preferably the bone anchor can angulate through a range of angles from about −25° to about +25° relative to the longitudinal axis of the connector body.

In one embodiment, the connector body has a pair of arms preferably shaped as cylindrical segments facing one another across the channel. Each arm preferably has curved opposite edge surfaces, a rim projecting radially inward, and a recess or notch in the rim. The cap is generally circular or disk-like, and preferably has a pair of bosses projecting radially outward. The cap optionally further has a pair of stoppers projecting radially outward and optionally a set of flanges projecting radially outward. In this example, the cap is receivable in the channel in a partially installed position in which the bosses, stoppers, and flanges are located in the space between the arms on the connector body. The cap is rotatable from the partially installed position to an installed position in which the bosses are received in the recesses, each stopper abuts or is in close proximity to a side edge of an arm, and the flanges are located beneath the rim. Preferably, the cap moves from the partially installed position to the installed position by rotating the cap, preferably without further axial movement as it is rotated.

In the case of a polyaxial connector body, which has a socket for insertion, angulation, and removal of the bone anchor, a sleeve may fit over the connector body in a temporary position in which it permits insertion of the bone anchor into the socket. The sleeve can advance from the temporary position to a locking position in which it blocks both angulation and removal of the bone anchor. The sleeve may be restrained from axial and rotational movement relative to the connector body when in the temporary position. The sleeve is preferably placed in the temporary position before the connector device is shipped to and/or handled by a surgeon. A surgeon may place the bone anchor into position on the spine, for example, a bone screw may be inserted into a vertebra, and thereafter the connector body may be snapped onto the bone anchor. The ability to place the bone anchor without the connector body attached may provide better visualization while inserting the bone anchor and it may be easier to insert the bone anchor into the vertebrae.

In one embodiment, the apparatus for connecting a bone anchor to a support rod comprises a connector body having a top opening, two opposed arms and a channel to receive and locate the support rod relative to the bone anchor, the channel communicating with the top opening, and a cap to secure the support rod in the channel. The cap preferably has one or more radial projections and the cap is configured to move axially into the top opening of the connector body into a partially installed position covering the top opening, and configured to thereafter rotate to an installed position without moving axially relative the connector body, whereby the one or more projections contact and deflect one or more of the arms outward to enlarge the top opening as the cap rotates toward the installed position. Preferably, the cap is movable axially into the partially installed position without rotating relative to the connector body. Each connector body arm preferably has at least one recess, and the cap's one or more radial projections are configured to fit or snap into at least one of the recesses when the cap is rotated into the installed position. More preferably the cap has at least two radial projections spaced approximately 180° from each other and the arms preferably are configured to deflect radially outward under the influence of the projections when the cap is rotated toward the installed position, and to snap back inward to capture the projections in the recesses when the cap reaches the installed position.

The cap preferably non-threadingly attaches to the connector body. The connector body preferably has arms shaped as cylindrical segments with radially extending rims, the cap has radially projecting flanges that are located circumferentially between the arms when the cap is in the partially installed position, and the flanges are configured to move circumferentially beneath the rims preferably without camming action when the cap is rotated toward and into the installed position. The cap preferably is rotated about 90° from the partially installed position to the installed position. The radially extending rims preferably contain recesses and the cap has radial projections configured to snap into the recesses when the cap is rotated into the installed position, and the cap preferably further has the radially projecting flanges configured to move circumferentially beneath the rims when the cap is rotated toward and into the installed position.

The cap optionally may include one or more radially projecting stoppers configured to move into abutment with or proximity to the connector body to block continued rotation of the cap beyond the installed position. The cap may comprises a ring and a set screw threadably mounted in the ring. In one embodiment, the connector body may have a bottom opening and is configured to receive at least a portion of the bone anchor through the bottom opening. In other embodiments, the connector body may be integral with the bone anchor. In use, the connector body and cap are interconnected as an assembly with a support rod in the channel, and further includes a plurality of such assemblies that are spaced apart from each other along the length of the support rod.

In yet another embodiment, an apparatus for connecting a bone anchor to a support rod, comprises (i) a connector body having a channel to receive and locate the support rod relative to the bone anchor, the connector body having two arms shaped as cylindrical segments facing across the channel, with each arm having a radially extending rim containing a recess, and (ii) a cap to secure the support rod in the channel, the cap having projections and flanges projecting radially outward from its periphery, the cap being configured to be freely movable axially into the channel to a partially installed position in which the projections and the flanges are located circumferentially between the arms, and the cap being further configured to attach to the arms by rotating from the partially installed position to an installed position in which the projections are located in the recesses and the flanges located beneath the rims. Preferably, each flange comprises a length extending about 90° of the cap. The cap projections preferably are located above a middle portion of the flange.

The connector body preferably is configured for the arms to deflect radially outward under the influence of the projections when the cap is rotated toward the installed position, and to snap back inward to capture the projections in the recesses when the cap reaches the installed position. The arms are located in the rotational path of movement of the flanges when the cap is in the partially installed position, and the projections are configured to deflect the arms radially outward to provide clearance for the flanges to move beneath the rims without interference when the cap is rotated toward and into the installed position. The recesses are optionally located in central portions of the rims.

Optionally, the connector body may include a sleeve surrounding at least a portion of the connector body. The sleeve preferably is configured to fit over the connector body in a temporary position in which the sleeve permits insertion of the bone anchor, preferably the sleeve is movable to a provisional locking position in which the sleeve permits angulation but prevents removal of the bone anchor, and preferably the sleeve is moveable to a locking position in which the sleeve prevents both angulation and removal of the bone anchor.

In yet another embodiment, the device for connecting a bone anchor to a support rod includes a connector body having a channel for receiving and locating the support rod relative to the bone anchor, the connector body having a pair of arms shaped as curved segments facing across the channel, with each arm having opposite side edge surfaces, a rim projecting radially inward, and a recess in the rim, and a generally circular cap to secure the support rod in the channel, the cap having a pair of bosses projecting radially outward, a pair of stoppers projecting radially outward, and a pair of flanges projecting radially outward, the cap being receivable in the channel in a partially installed position in which the bosses, stoppers and flanges are located circumferentially between the arms on the connector body, and being rotatable from the partially installed position to an installed position in which the bosses are received in the recesses, each stopper abuts or is in proximity to the side edge of an arm, and the flanges are located beneath the rims. The bosses preferably project radially outward sufficiently to move against side edges of the arms to deflect the arms radially outward upon rotation of the cap from the partially installed position toward the installed position, and are sized to fit, preferably completely, within the recesses so that the arms will return to their original undeflected conditions when the cap reaches the installed position. The bosses also preferably project radially outward in diametrically opposed positions on the cap, the stoppers project radially outward in diametrically opposed positions on the cap that are circumferentially offset about 45 degrees from the bosses, and the flanges extend about 90 degrees about the periphery of the cap.

The bone connecting device in a further embodiment includes (i) a connector body having a bottom opening, a channel to receive the support rod and a socket for insertion, angulation, and removal of the bone anchor, the socket in communication with the bottom opening, and (ii) a sleeve configured to fit over the connector body in a temporary position in which the sleeve permits insertion of the bone anchor, the sleeve configured to move to a provisional locking position in which the sleeve permits angulation but prevents removal of the bone anchor, and the sleeve configured to move to a locking position in which the sleeve prevents both angulation and removal of the bone anchor. The sleeve is optionally configured to engage the connector body so as to be restrained from axial and rotational movement relative to the connector body when in the temporary position. The sleeve may be configured to engage the connector body in an interference fit in the temporary position. The sleeve may have inner flanges configured to establish the interference fit with the connector body.

The sleeve may be further configured to fit over the connector body in a preliminary position in which the sleeve is freely movable axially and rotationally relative to the connector body, and the sleeve may be configured to be axially moveable to the temporary position. The connector body preferably has a substantially cylindrical outer surface with radially raised step portions, and the sleeve preferably has inner retainer portions that are moveable axially against the step portions of the cylindrical outer surface to establish an interference fit with the connector body upon movement of the sleeve axially from the preliminary position to the temporary position.

The sleeve may be configured (i) to be receivable over the connector body in a first preliminary position upon movement of the sleeve axially over the connector body in a first direction, (ii) to be rotated from the first preliminary position to a second preliminary position, and (iii) to move from the second preliminary position to the temporary position, onward to the provisional locking position, and further to the locking position upon movement of the sleeve axially over the connector body in a second direction opposite the first direction. In use, the connector body and sleeve are interconnected in an assembly mounted on the bone anchor with a support rod in the channel, and further may comprise a plurality of such assemblies that are spaced apart from each other along the length of the support rod.

The sleeve may be receivable over the connector body in a locking position in which the sleeve prevents angulation and removal of the bone anchor from the socket, the sleeve preferably having inwardly projecting retainer flanges receivable against the connector body in an interference fit from which the sleeve is releasable for movement toward the locking position. The connector body may have a substantially cylindrical outer surface with radially raised step portions, and the retainer flanges may be deflectable to enlarged inner diameters to establish the interference fit upon moving axially onto the step portions of the cylindrical outer surface. The step portions of the cylindrical outer surface may be upper step portions and the substantially cylindrical outer surface further may have lower step portions that are raised radially outward from the upper step portions, and the retainer flanges are deflectable to further enlarged inner diameters upon moving axially onto the lower step portions. The substantially cylindrical outer surface may have axially extending grooves located circumferentially between the step portions. The flanges may be configured and arranged so that the flanges may move axially in the grooves without interference with the connector body. The connector body may have a lower section and a middle section, the lower section preferably contains the socket and the middle section preferably contains the substantially cylindrical outer surface, the connector body further may have a concave transition portion between the lower and middle sections, and the projecting retainer flanges may be receivable in the concave transition portion to prevent the sleeve from moving axially and contacting the substantially cylindrical outer surface.

The invention further provides tools for installing the connector body, cap, and support rod. The tools may include a tube that provides a passageway that may guide the cap toward and into engagement with the connector body.

Once the connector body has been clicked onto the bone anchor, there are two techniques to install the support rod.

1. Insertion of the support rod into the U-shaped channel of the connector body prior to the installation of the tools used to guide the cap toward and into engagement with the connector body. The tools used to insert the support rod may have means to push the rod into position and restrain movement of the rod relative to the connector prior to the installation of the cap to enhance the insertion of the cap.

2. Insertion of the support rod after installation of the tools used to guide the cap toward and into engagement with the connector body. The tube providing a passageway for the cap may have a slot to receive the support rod transversely through the tube and may have means to restrain movement of the rod relative to the connector body prior to the installation of the cap.

One such tool for connecting a bone anchor assembly to a support rod, wherein the bone anchor assembly has a connector body with a channel to receive the support rod, and has a cap receivable on the connector body in an installed position to secure the support rod in the channel, comprises a tube having a distal end, a proximal end, an opening at each end, and an axial passageway in communication with the openings, the tube configured to guide the cap toward and into engagement with the connector body upon movement of the cap longitudinally through the axial passageway of the tube; the tube further having two collateral recesses at the proximal end to receive the support rod already loosely placed in the channel of the connector body and two collateral projections lateral to the recesses fitting in-between the support rod and the connector body. Rotating the tube, the projections may get engaged with the connector body, thus, a force may be exerted on the rod by the tube pushing the rod into place and restraining movement of the rod relative to the connector body. Depending on the geometry of the collateral recesses, the connector body may actively be pulled up to the support rod allowing corrections of the spine.

Another tool for connecting a bone anchor assembly to a support rod, wherein the bone anchor assembly has a connector body with a channel to receive the support rod, and has a cap receivable on the connector body in an installed position to secure the support rod in the channel, comprises a tube having a distal end, a proximal end, an opening at each end, and an axial passageway in communication with the openings, the tube configured to guide the cap toward and into engagement with the connector body upon movement of the cap longitudinally through the axial passageway of the tube, the tube further having a slot at and transverse to the distal end to receive the support rod, and being further configured to interconnect the support rod with the tube and the connector body prior to installation of the cap. The tube may be receivable over the connector body in a first orientation in which the support rod is movable downward through the slot toward and into the channel, and the tube may be movable relative to the connector body to a second orientation in which the tube blocks movement of the support rod upward within the channel. The tube may be rotatable from the first orientation to the second orientation. The tube may have surfaces that extend transversely from the slot in opposite directions so as to move circumferentially over the support rod upon rotation of the tube from the first orientation to the second orientation. The tube and the connector body together may be configured to block movement of the tube upward relative to the connector body when the tube is in the second orientation. The connector body may have cylindrical segments with downwardly facing blocking portions, and the tube may have cylindrical segments with upwardly facing blocking portions configured to move under the downwardly facing blocking portions upon rotation of the tube from the first orientation to the second orientation.

A system of tools for connecting a bone anchor assembly to a bone support rod wherein the bone anchor assembly has a bone anchor, a connector body and a sleeve, the connector body has a channel to receive the bone support rod and a socket to receive the bone anchor, and the sleeve is movable axially over the connector body into a locking position to secure the bone anchor in the socket is also disclosed, the system may comprise: (i) a tube having a distal end, a proximal end, an opening at each end, and an axial passageway in communication with the openings, the tube receivable over the connector body and having a slot to receive the bone support rod; and (ii) an elongated tool receivable within the axial passageway of the tube and configured to interlock axially with the connector body inside the tube, whereby the elongated tool can apply a force axially against the connector body in reaction to a force urging the sleeve axially toward the locking position. The elongated tool may be configured to interlock axially with the connector body upon rotating relative to the connector body and the tube. The elongated tool may have cylindrical segments that are rotatable into axially interlocked engagement with the connector body. The connector body may have cylindrically contoured arms at which the segments of the elongated tool interlock with the connector body. The system may further comprise a pusher tool movable telescopically within the tube toward and into engagement with the sleeve to apply a force axially downward against the sleeve when the elongated tool is interlocked with the connector body within the tube. The system may further comprise a hand-held actuator operative to apply a force axially upward against the elongated tool and simultaneously to apply a force axially downward against the pusher tool.

A system for connecting a bone anchor assembly to a support rod wherein the bone anchor assembly has a connector body with a channel to receive the support rod, and has a cap configured to fit on the connector body in an installed position to secure the support rod in the channel is also disclosed, the system comprising: (i) a tube having a distal end, a proximal end, an opening at each end, and an axial passageway in communication with the openings, the tube configured to guide the cap toward and into engagement with the connector body upon movement of the cap through the tube; and (ii) a cap holder configured to carry the cap through the axial passageway of the tube and to place the cap in the installed position on the connector body, wherein the cap and the cap holder have screw threads for screwing the cap holder into attachment with the cap outside of the tube and for unscrewing the cap holder from the cap inside the tube. The cap may include a set screw with an external screw thread, and the cap holder may have an internal screw thread for mating with the external screw thread.

An apparatus or system for connecting a bone anchor assembly to a support rod, wherein the bone anchor assembly has a connector body with arms and a channel to receive the support rod between the arms, and further has a cap configured to fit on the connector body in an installed position in which a screw on the cap can be tightened against the support rod in the channel is also disclosed, the apparatus or system may comprise: a counter-torque instrument configured to restrain the cap from moving under the influence of torque transmitted from the set screw to the cap, the counter-torque instrument having segments configured to fit between the flanges of the cap to restrain the cap from rotating. The system may further comprise a guide tube configured to guide the cap toward and into engagement with the connector body upon movement of the cap through the guide tube, and a cap holder configured to carry the cap through the guide tube and to place the cap in the installed position on the connector body, wherein the counter-torque instrument includes an insertion tube receivable within the guide tube and through which the cap is movable by the cap holder. The counter-torque instrument may have a handle projecting laterally from the insertion tube.

A system for connecting a bone anchor assembly to a support rod wherein the bone anchor assembly has a bone anchor, a connector body, a sleeve and a cap, the connector body has a channel to receive the support rod and a socket for angulation of the bone anchor, the sleeve is configured to fit over the connector body in a locking position in which the sleeve blocks angulation of the bone anchor, and the cap is receivable on the connector body in an installed position securing the bone support rod in the channel is also disclosed, the system may comprise: (i) a tube configured to guide the cap toward and into engagement with the connector body upon movement of the cap longitudinally through the tube, the tube having a slot to receive the bone support rod through the tube, and being further configured to interlock the bone support rod with the connector body prior to installation of the cap; and (ii) an elongated tool receivable within the tube and configured to interlock axially with the connector body inside the tube, whereby the elongated tool can apply a force axially against the connector body in reaction to a force urging the sleeve axially toward the locking position. The system may further comprise a cap holder configured to carry the cap through the tube and to place the cap in the installed position on the connector body, wherein the cap and the cap holder have screw threads for screwing the cap holder into attachment with the cap outside of the tube and for unscrewing the cap holder from the cap inside the tube. The system may further comprise a counter-torque instrument configured to restrain the cap from moving under the influence of torque transmitted from the set screw to the cap, the counter-torque instrument having cylindrically contoured segments configured to fit between the flanges of the cap to restrain the cap from rotating.

Another tool may actuate the sleeve on the connector body. This other tool may fit within the tube to interlock axially with the connector body inside the tube. When interlocked with the connector body, the elongated tool can apply a force upward against the connector body in reaction to a force urging the sleeve downward toward the locking position.

Additional installation tools may include a holder that carries the cap through the tube to place the cap in the installed position on the connector body, and a counter-torque instrument that restrains the connector body from rotating under the influence of torque transmitted from the cap. It should be recognized that one or more of the tools may be included in a kit.

BRIEF DESCRIPTION OF THE DRAWINGS

FIG. 1 is a perspective view of a bone fixation assembly.
FIG. 2 is a side view of the bone fixation assembly shown in FIG. 1.
FIG. 4 is a top view of the connector body of FIG. 3.
FIG. 5 is a sectional view taken along line 5-5 of FIG. 4.
FIG. 6 is an upper perspective view of a sleeve, which also is one of the parts of the bone fixation assembly shown in FIGS. 1 and 2.
FIG. 7 is a top view of the sleeve.
FIG. 8 is a sectional view taken on line 8-8 of FIG. 7.
FIGS. 9*a*, 9*b*, and 10 are sectional views showing the connector body and the sleeve in different positions.
FIGS. 11 and 12 are sectional views showing a bone anchor with the connector body and the sleeve in different positions.

FIG. 13 is an upper perspective view of a locking ring, which is another part of the bone fixation assembly shown in FIGS. 1 and 2.

FIG. 14 is a lower perspective view of the locking ring.

FIG. 15 is a top view of the locking ring.

FIGS. 16-18 are top views showing sequential positions taken by the locking ring upon installation on the connector body.

FIG. 19 is a longitudinal cross-section of a side loading connector body and sleeve, with the sleeve in a temporary position to permit the bone anchor to be inserted into the connector body.

FIG. 20 is a view of the side loading connector body and sleeve of FIG. 19 but showing the sleeve moved to a provisional locking position where the bone anchor is retained in the connector body but is free to angulate with respect to the connector body.

FIG. 28 is an enlarged partial side view of the part shown in FIG. 26.

FIG. 29 is a view taken along line 29-29 of FIG. 28.

FIG. 30 is a view taken along line 30-30 of FIG. 28.

FIG. 39 is a view similar to FIG. 36 showing additional parts.

FIG. 40 also is a view similar to FIG. 36 showing additional parts.

FIG. 41 is a view similar to the view of FIG. 40 showing parts in different positions.

FIGS. 42 and 43 are side views of another installation tool.

FIG. 44 is a side view of yet another installation tool.

DETAILED DESCRIPTION

Figure 3:
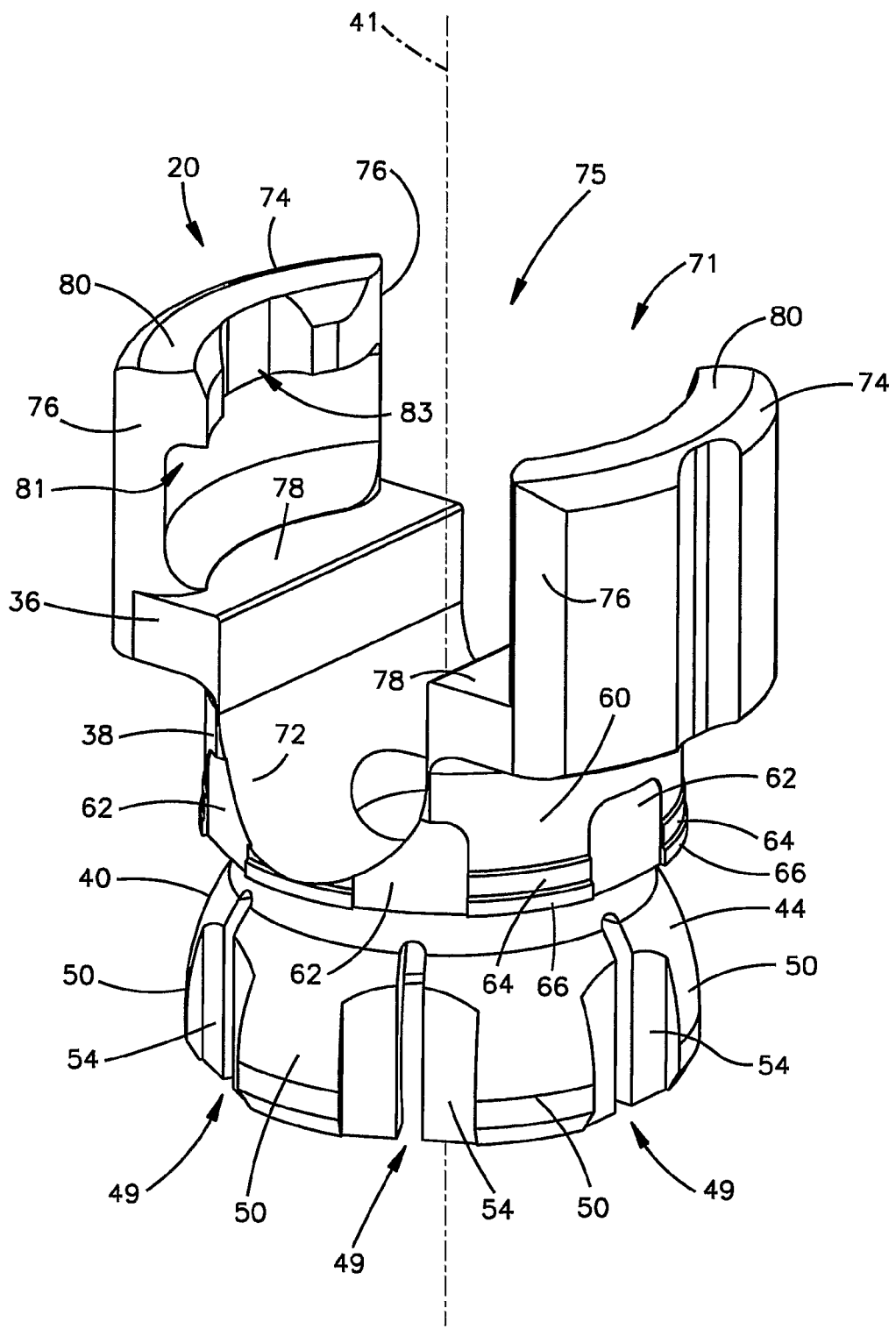
FIG. 3 is an enlarged perspective view of a top loading connector body, which is one of the parts of the bone fixation assembly shown in FIGS. 1 and 2.

The drawings include examples of a bone fixation system and tools and instruments to assist in the implantation of the system. The drawings and description are merely exemplary to illustrate features, parts and tools that may be used singularly or in combination with other features, and the present invention should not be limited to the embodiments shown. The parts shown in the drawings include examples of how a person of ordinary skill in the art can make and use the claimed invention and are provided and described herein for enablement and best mode purposes and should not be used to impose limitations that are not recited in the claims.

A connector device 10 is shown in FIGS. 1 and 2. The connector device 10 is an assembly of parts for interconnecting a bone anchor 12 with a bone support device 14. In this particular example, the support device 14 is a spinal rod, and the anchor 12 may be one of several pedicle screws implanted in vertebrae preferably in a row extending along the length of the spine. The connector device 10 may thus be one in a corresponding row of connector devices that rigidly interconnect the pedicle screws 12 with the rod 14.

The device 10 shown in FIGS. 1 and 2 includes a connector body 20 that is mounted on the head 22 of the bone anchor 12. While the bone anchor 12 is illustrated as a bone screw, it may also be a hook, pin, or other fastener. When the body 20 is first mounted on the head 22 it may rotate or pivot polyaxially relative to the screw 12. This type of movement, which is known as angulation, enables the body 20 to be adjusted into alignment with the other bodies 20 in the other devices 10 that are spaced apart along the length of the spine. FIGS. 1 and 2 illustrate a top loading connector body 20 but other connector bodies such as side loading or closed connector bodies also may be used. The rod 14 may be restrained by or attached to the row of aligned bodies 20. Although the illustrated bone anchor 12 is a separate part upon which the connector body 20 is mounted for polyaxial movement, alternative embodiments may include a monoaxial bone anchor which, as known in the art, is a bone anchor that has a connector body integral with and monolithic with the bone anchor.

Other parts of the device 10 may include a cap 30 and a sleeve 32. The cap 30 retains the rod 14 within the body 20. Specifically, the cap 30 is installed in the body 20 over the rod 14, and preferably includes a locking ring that attaches to the connector body and a set screw 34 that is tightened downward against the rod 14. The locking ring preferably attaches to the connector body but preferably does not lock the rod or bone anchor relative to the connector body. Preferably, when the set screw 34 is tightened against the rod 14, it clamps the rod 14 firmly between the locking cap 30 and the sleeve 32. This restrains the rod 14 from moving relative to the body 20. Tightening the set screw also pushes the sleeve 32 downward to a locking position which prevents further angulation of the body 20 on the pedicle screw 12.

As shown separately in FIGS. 3-5, the connector body 20 is a vertically elongated part with upper, middle, and lower sections 36, 38 and 40 centered on a longitudinal axis 41. The lower section 40 of the body 20 preferably has inner and outer surfaces 42 and 44 preferably with spherical contours. Preferably, the exterior surface 44 of the lower section 40 is at least part spherical. The inner surface 42 has a chamfered edge 46, and defines a socket or chamber 47 for receiving the head 22 of the pedicle screw 12 (FIG. 2). A bottom opening 48 communicates with the socket 47.

While the inner surface 42 of the socket 47 preferably has spherical contours to mate with the partially spherical contour of the illustrated pedicle screw 12, the inner surface 42 may have conical contours or other shapes, and the head of the bone anchor 12 may also have a conical contour or other shape. Slots 49 extend axially upward to separate the lower section 40 into segments 50. In the illustrated example the slots 49 are spaced apart at 60° intervals about the axis 41, as are the corresponding segments 50. Preferably, six slots are equidistantly spaced around the circumference of the loser section 40. The slots 49 may be evenly or unevenly spaced, and may be spaced at different angular intervals. The slots 49 enable the segments 50 to deflect radially outward when the chamfered edge 46 is pressed forcefully downward over the bone anchor head 22, and to shift radially back inward to capture the screw head 22 in the socket 47. The lower section 40 preferably forms an open ended chamber that is part spherical in shape and which is expandable and compressible to receive the preferably geometrically complementary head of a bone anchor. When the segments are in their unbiased natural state, the bottom opening 48 at the edges 46 is smaller than the largest diameter of the head of the bone anchor.

As best shown in FIG. 3, the outer surface 44 is interrupted by recessed flats 54 that preferably traverse the slots 49. As best shown in FIG. 5, the outer surface 44 has a concave portion 56 defining a transition between the lower and middle sections 40 and 38 of the body 20. The middle section 38 has a cylindrical outer surface 60 that is similarly interrupted by recessed flats 62 in alignment with the flats 54 in the lower section 40. Upper and lower step portions 64 and 66 of the cylindrical outer surface 60 are raised radially and extend circumferentially between the flats 62.

The middle and upper sections 38 and 36 of the body 20 together define a generally U-shaped channel 71 for receiving the spinal fixation device 14 and the cap 30. The axis of the channel 71 is generally perpendicular to the longitudinal axis 41 of the connector body 20. The axis of the channel 71 preferably intersects the axis 41 of the connector body, but may be offset or eccentric thereto. A trough-shaped inner surface 72 extends across the bottom of the channel 71. A pair of arms 74 at the upper section 36 define a top opening 75 communicating with the channel 71. The arms 74 preferably are configured as diametrically opposed curved or cylindrical segments facing each other across the channel 71.

The arms 74 are alike, and each has a length extending approximately 90° about the axis 41 between a pair of circumferentially opposite edge surfaces 76. Each arm 74 further has a planar shoulder surface 78 facing axially upward within the channel 71, and has a rim 80 projecting inward at its upper end. Each rim 80 preferably has a rounded inside corner defining a groove 81 that extends across the arm 74 between the opposite edge surfaces 76. Each rim 80 also has a notch or recess 83 preferably mid-way between the opposite edge surfaces 76.

The connector device preferably has a locking means for clamping the bone anchor relative to the connector body. The locking means preferably is axially moveable relative to the lower section of the connector such that in a temporary position the socket or chamber can expand resiliently to receive the head of the bone anchor preferably in a click-on or snap-on action, but in a provisional locking position, the chamber can no longer expand. The locking means preferably is moveable into a further position where it bears against the outside surface of the lower section defining the socket to compress segments 50 around the head of the bone anchor to prevent movement between the bone anchor and the connector.

The locking means preferably comprises a sleeve at least partially located around and moveable over the lower section 40 of the connector. As shown separately in FIGS. 6-8, the sleeve 32 may be a short cylindrical part with a longitudinal central axis 89 and is preferably configured to operate in a two-stage locking operation. The sleeve 32 assists with locking the position of the bone anchor 12 relative to the connector body 20. Preferably, a pair of recessed surfaces 90 at the open upper end 91 of the sleeve 32 are aligned as seats for the rod 14 (FIGS. 1 and 2). Guide flanges 92 and retainer flanges 94 at the interior of the sleeve 32 are configured for the manner in which the sleeve 32 fits over the connector body 20. The guide flanges 92 project radially inward at the upper end 91 of the sleeve 32, and are arranged in diametrically opposed pairs. As with the slots 49 in the body 20 (FIG. 3), there are preferably six guide flanges 92 preferably spaced apart at 60° intervals.

The guide flanges 92 have a common inner diameter that preferably is slightly greater than the outer diameter of the body 20 at the cylindrical surface 66. The retainer flanges 94 project radially inward at locations directly beneath the guide flanges 92, and also have a common inner diameter. The inner diameter of the retainer flanges 94 preferably is slightly greater than outer diameter at the flats 62 in the cylindrical surface 60 slightly less than the inner diameter of the guide flanges 92, and slightly less than the outer diameter of the cylindrical surface 64. To provide enough space for the retainer flanges 94 during the installation of sleeve 32, the distance between two collateral flats 54 is slightly less than the inner diameter of the retainer flanges 94.

In addition to the flanges 92 and 94 for engaging the middle section 38 of the body 20, the sleeve 32 has inner surfaces 100 and 102 for engaging the lower section 40 of the body 20. The first inner surface 100 has a cylindrical contour centered on the axis 89. The second inner surface 102 extends axially upward from the first inner surface 100 with a conical contour that tapers radially inward. The conical inner surface 102 is slidable over the outer surface of the lower section 40 to compress the chamber 47 to lock the bone anchor relative to the connector body 20. Preferably, contact between the spherical outer surface of the lower section of the connector body and the conical inner wall of the sleeve is tangential to the spherical outer surface of the lower section 40.

Figure 10:
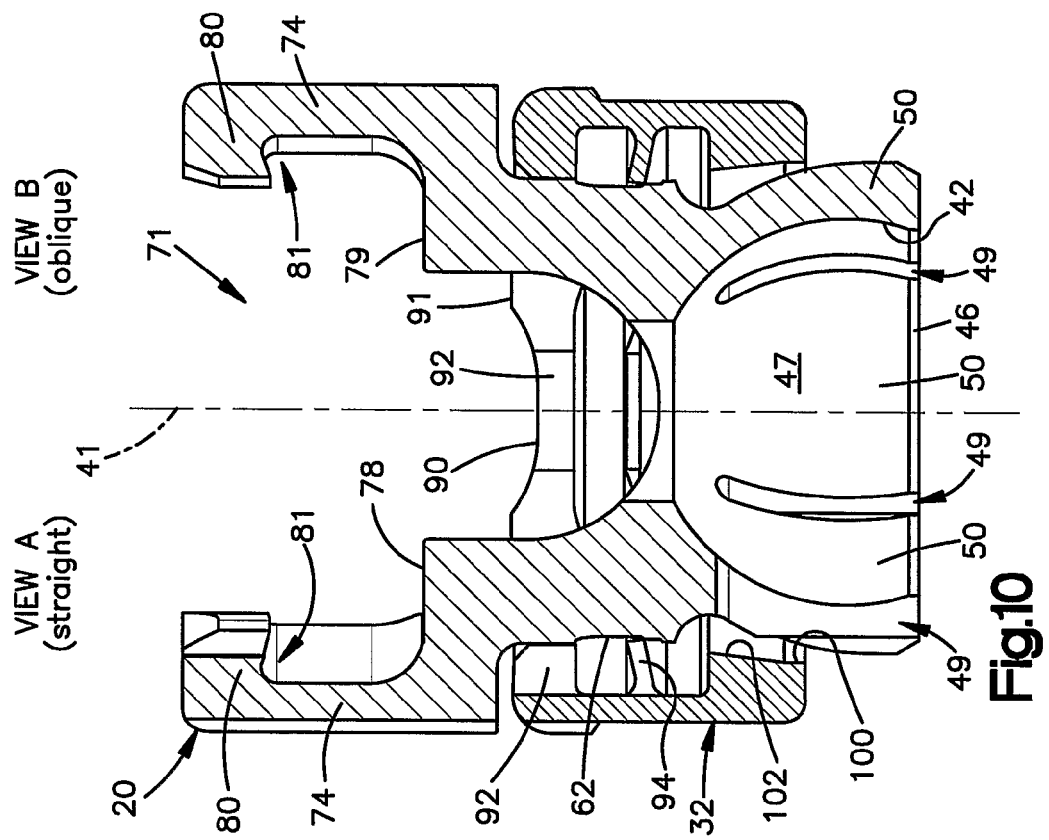

To attach the sleeve to the body connector, the sleeve 32 is placed over the body 20 by aligning the flanges 92 and 94 of the sleeve 32 with the flats 54 and 62 and moving the upper end 91 of the sleeve upward over the lower section 40 of the body 20 from beneath into the first preliminary position (FIG. 9a), thereby temporarily compressing the segments 50. The flats 54 and 62 on the body 20 guide the sleeve 32 by providing grooves, pathways or space along which the flanges 92 and 94 are axially movable over the body 20. When the sleeve 32 reaches a first preliminary position, as shown in FIG. 9a, the flanges 92 and 94 are located at the flats 62 on the cylindrical surface 60. The sleeve 32 is next rotated, preferably 30°, from the first preliminary position until the collateral recesses 90 on top of the sleeve 32 are aligned with the U-shaped channel 71 of the body 20 (FIG. 9b), and then pushing the sleeve 32 down into the second preliminary position. This moves the flanges 92 and 94 to a position in which they are located between the flats 62 and above the step portions 64 and 66, as shown in FIG. 10 (oblique view). The flanges 92 and 94 preferably do not yet engage the cylindrical surface 60 tightly enough to restrain axial or rotational movement of the sleeve 32 relative to the body 20.

The sleeve 32 is next moved downward from the second preliminary position until the retainer flanges 94 move axially onto the upper step portions 64 of the cylindrical surface 60. This causes the retainer flanges 94 to bear against upper step portions 64 and deflect to enlarged inner diameters at which they establish an interference fit with the upper step portions 64, as shown in FIGS. 10 and 11. The interference fit restrains the sleeve 32 from moving axially or rotationally relative to the body 20. In this manner the sleeve 32 is conveniently retained on the body 20 in a temporary position for later advancement to the locking position in which it prevents angulation of the body 20 relative to the bone anchor. The lower step portion 66 of the cylindrical surface 60, which is raised radially from the upper step portion 64, blocks the sleeve from being inadvertently moved further downward. Preferably, the sleeve 32 is placed in the temporary position before the connector device 10 is shipped to and/or handled by a surgeon. While the sleeve 32 is retained in the temporary position of FIG. 11, the inner surfaces 100 and 102 are spaced from the outer surface 44 of the body 20 and the segments 50 of the body 20 are free to deflect radially outward for insertion of the pedicle screw head 22 into the socket 47. With the sleeve in the temporary position, the bone anchor can also be dislodged from the socket 47.

When the sleeve 32 is moved further downward, the retainer flanges 94 on the sleeve 32 are deflected to further enlarged inner diameters as they move onto the lower step portions 66 of the cylindrical surface, and then snap back toward their original inner diameters as they move axially over and downward past the lower step portions 66. In this position, the retainer flanges no longer bear against the step portions 64 or 66 but occupy the gap created by the transition 56. The transition 56 captures the retainer flanges 94 to block the sleeve 32 from moving back upward. When the sleeve 32 is in the position shown in FIG. 12, with the bottom inner surface 100 of the sleeve 32 closely surrounding the outer surface 44 of the body 20, it is in a provisional locking position. In the provisional locking position, the upper annular surface 95 of the sleeve preferably is adjacent the step portions 64,66 and in loose contact with the cylindrical surface 60. In the provisional locking position, the sleeve 32 prevents removal of the screw head 22 from the socket 47 by blocking the segments 50 from deflecting radially outward. However, the sleeve 32 does not yet engage or bear against the segments 50 tightly enough to prevent continued angulation of the body 20 on the screw head 22. Angulation is not prevented until the sleeve 32 is later pushed downward from the provisional locking position to the locking position, at which time the tapered contour of the second inner surface 102 causes the sleeve 32 to press radially inward against the segments 50 tightly enough to clamp the screw head 22 firmly within the socket 47.

The cap 30 preferably includes set screw 34 and a locking ring 120 (shown separately in FIGS. 13-15). The inner periphery of the ring 120 defines a bore 121 with a central axis 123 and an internal screw thread 124 for receiving the set screw 34. The outer periphery 131 of the ring 120 is configured to mate with the arms 74 of the connector body 20. The outer periphery 131 preferably includes a pair of projections (also referred to as bosses) 126 projecting radially outward in diametrically opposed positions to fit into the notches or recesses 83 in the arms 74. The projections or bosses 126 preferably have a curved surface 129. A pair of stoppers 128 project radially outward in positions that are circumferentially offset from the bosses 126 approximately 45° about the axis 123. The stoppers preferably have curved leading edges 129.

Located below the bosses 126 and stoppers 128 are two flanges 130 that are sized and shaped to fit beneath the rims 80 on the arms 74. Each flange 130 on the ring 120 has a length extending approximately 90° about the axis 123 from a leading end 132 to a trailing end 134. An upper edge 136 of each flange 130 has a rounded contour preferably substantially matching the rounded contours of the grooves, pathways or space 81 in the arms 74. A lower portion 138 of each flange 130 projects downward next to the leading end 132. The lower portions 138 of the flanges 130 preferably have planar bottom surfaces 140 to sit on the planar shoulder surfaces 78 of the arms 74. The lower portions 138 form a part cylindrical profile on the underside of the ring 120 preferably to match the profile of the support rod to be retained by the connector. The lower portions are intended to reinforce the cap.

The cap 30 is installed on the connector body 20 by first placing it in the partially installed position shown in FIG. 16. The cap is operatively associated with the upper section 36 of the connector body 20. The projecting parts 126, 128 and 130 of the ring 120 are received in channel 71, and more specifically the spaces extending circumferentially between the arms 74. The bottom surfaces 140 preferably land on the shoulder surfaces 78. The ring 120 is freely movable coaxially downward between the arms 74 to take the partially installed position of FIG. 16 without rotating relative to the body 20, and is unattached to the body 20 in that position.

As viewed in FIGS. 16-18, the cap 30 preferably snaps into attachment with the connector body 20 when rotated approximately 90° clockwise from the partially installed position without moving axially relative to the body 20. Preferably, the arms 74 initially obstruct the rotational paths of movement of the bosses 126, and preferably flanges 130 on the ring 120. As the ring 120 rotates into and past the position of FIG. 17, the bosses 126, and more specifically, the preferred curved surface of the bosses 126 move against the adjacent edge surfaces 76 of the arms 74 to deflect the arms 74 radially outward, and, preferably, thereby provide clearance for the flanges 130 to move beneath the rims 80 as the bosses 126 slide along the rims 80 and the bottom surfaces 140 slide over the shoulder surfaces 78. The bosses 126 are sized to fit within the notches 83 so that the arms 74 will snap back inward to their original undeflected conditions to capture the bosses 126 in the notches 83 when the ring 120 reaches the installed position of FIG. 18. Further clockwise rotation of the ring 120 is blocked by the stoppers 128 in abutment with the side edge surfaces 76. The contours of the edges 136 (FIGS. 13-14) preferably are complementary to the contours in the grooves 81 (FIG. 5) to ensure a firm fit of the cap 30 in the body 20. At this point, the rod can be retained in the connector body but can still be moveable relative to the connector body, and the connector body can still be moved relative to the bone anchor. In this manner, a physician can still manipulate the bone fixation system since the bone anchor can move relative to the connector and the support rod has not been clamped in position.

Final locking of the connector and bone fixation system can be accomplished by using set screw 34. The support rod is moveable within the channel 71 by the set screw and is clamped therein by the set screw. The set screw 34 can be tightened downward against the spinal rod 14 to interlock the connector device 10 with the pedicle screw 12 and the rod 14. More specifically, the set screw urges the spinal rod against the sleeve to cause the sleeve to move down the connector body. As the sleeve moves down the body, the sleeve inner surface causes the sleeve to press radially inward against the segments 50 tightly enough to clamp the bone anchor in position. The set screw also clamps the rod tightly enough against the sleeve to hold the support rod in position.

The bone anchor also may be locked in the body 22 without or before insertion of the spinal rod in the body. For example, the sleeve may be pushed downward to the position shown in FIG. 12 without the spinal rod placed in the connector body. Before, or after insertion of the spinal rod, the sleeve may be moved down to press radially against segments 50 tightly enough to lock the position of the bone anchor. The support rod may also be used to move the sleeve down the connector body into the locked position without the cap being positioned on the connector body.

FIGS. 19-23 illustrate a side loading connector device 1000. Connector device 1000 comprises a body 1002 defining a first section 1003 for connection to the head 1004 of a bone anchor 1005. The first section 1003 is substantially similar to lower section 40 in connector body 20. The connector body 1002 also includes a second section 1006 adapted for connection to the support rod 1007 (show in cross-section in FIGS. 21-23). The second section 1006 is similar to upper and middle sections 36,38 of the connector body 20 except as described herein. The connector 1000 in addition comprises sleeve 1008 (which is substantially similar to or the same as sleeve 32), a cap 1009 and a retaining member 1010.

The second section 1006 of the body 1002 defines a laterally open channel 1019 for receiving the support rod 1007. It should be appreciated that in other embodiments of the connector, the longitudinal axes of the first and second sections of the connector may not be coincident. However, in this embodiment, the channel 1019 is oriented transversely and eccentrically with respect to the longitudinal axis 1012 of the body 1002 and the longitudinal axis of the second section 1006 is coincident with the longitudinal axis of the first section 1003. An outer thread 1020 is formed on an upper portion 1021 of the body 1002 which has a reduced diameter. The retaining member 1010 is adapted to be concentrically mounted around second section 1006 of the body 1002 between the sleeve 1008 and the cap 1009. The cap 1009 in this case is a tightening nut which is threaded on the screw thread 1020 and comprises a head 1022 that bears on the end of the retaining member and a depending retaining member portion 1023 that screws down the thread 1020 between the retaining member 1010 and the body 1002 owing to the reduced diameter of the body 1002 in this region.

Support rod 1007 becomes retained in place by the retainer member 1010 which closes off the channel 1019. When the locking cap 1009 is tightened to lock the connector into its final position, the head 1022 of the cap 1009 bears down on the retainer member 1010. The retainer member 1010 again is pressing down on the sleeve 1008 through the support rod 1007. The length of the depending portion 1023 is short enough that it will not interfere with the support rod 1007.

Being forced down by the retainer member 1010 and the support rod 1007, the sleeve 1008 moves down along the section 1003 of the body 1002 simultaneously compressing the chamber 1011 over the head 1004 of the bone anchor 1005, locking it in position, and clamping the support rod 1007. Preferably, the sleeve 1008 moves down until the support rod 1007 is stopped by the bottom of the channel 1019.

Figure 21:
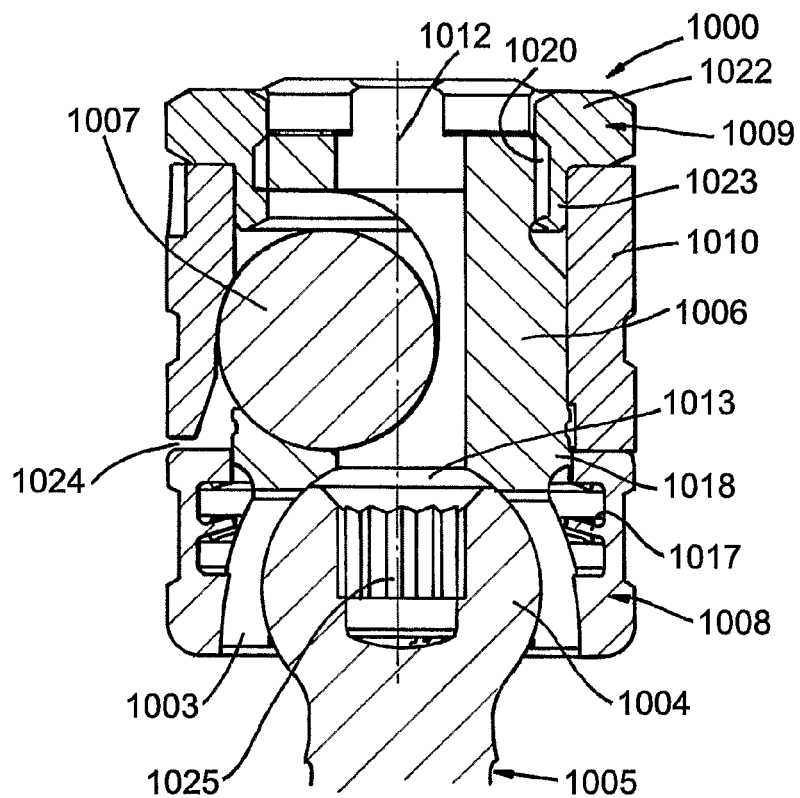
FIG. 21 is a longitudinal cross-section of the connector body and sleeve shown in FIGS. 19 and 20, together with a support rod, bone anchor, cap and retaining members after locking the connector to the bone anchor.
Figure 22:
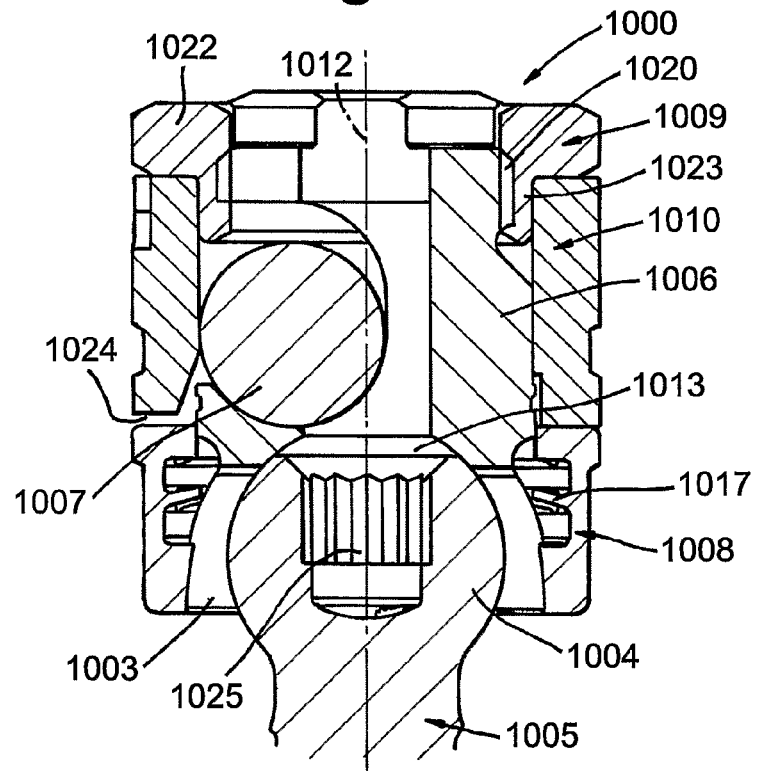
FIGS. 22 and 23 are views similar to FIG. 21 but with modified connector bodies adapted for use with support rods of a different diameter.
Figure 23:
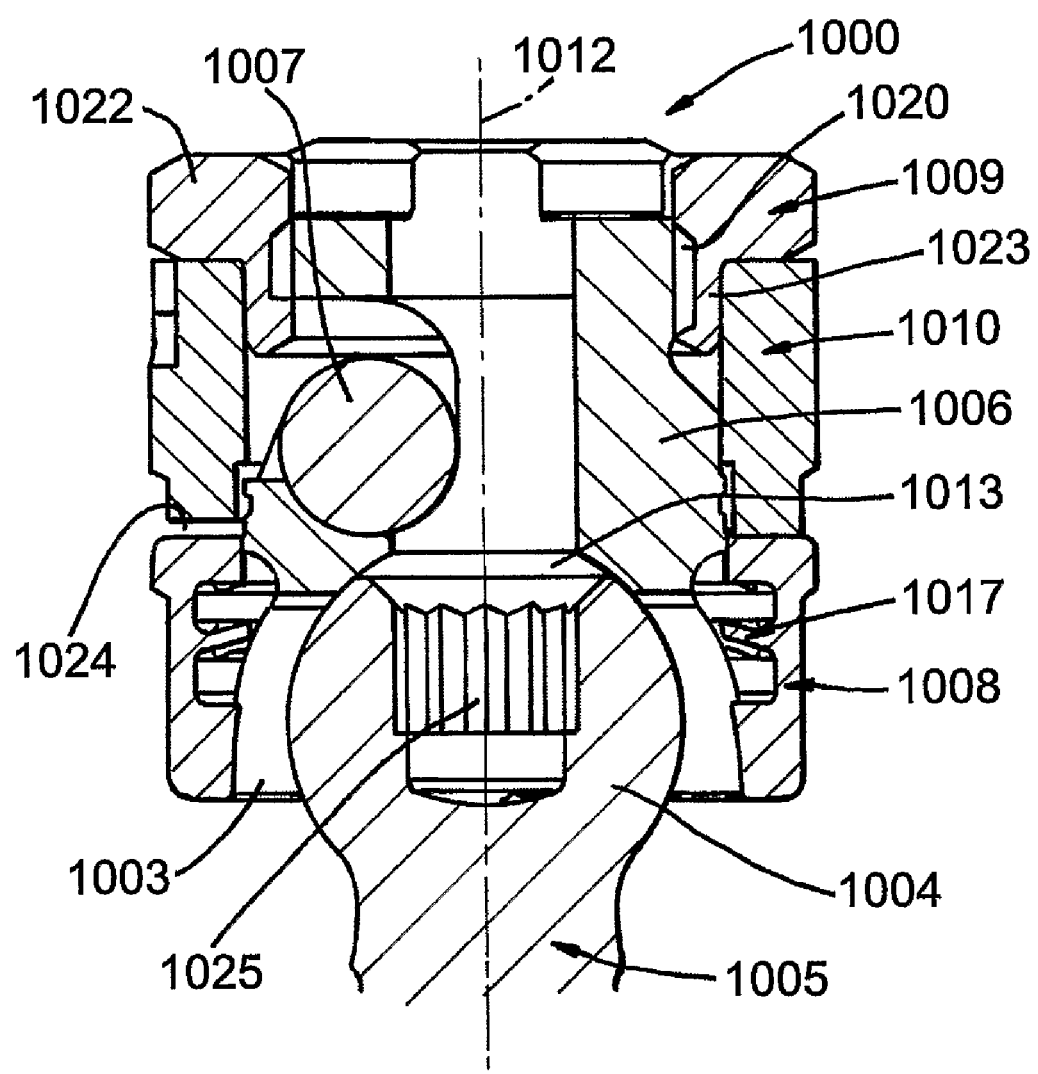

It can be seen in FIGS. 21-23 that the sides of the retaining member 1010 on either side of the channel 1019 are of different heights such that when the connector 1000 has been locked using the locking cap 1009, a small gap 1024 of around 0.3 nm is left between the face of the first annular portion of the sleeve 1008 and the lower edge of one side of the retaining member 1010. The different heights on the two side of the retaining member 1010 are dimensioned such that when cap 1009 is tightened, only the support rod 1007 and the longer side of the retaining member 1010 press against sleeve 1008. Hence, the clamping force exerted by cap 1009 is distributed to three contact zones on the sleeve 1008, which are arranged such that they apply uniform pressure to the sleeve 1008 in a plane substantially perpendicular to the axis 1012. As a result, the sleeve 1008 is maintained coaxially aligned over the spherical outer surface of the section 1003 of the body 1000 and therefore uniformly compresses the chamber 1011. Also, the contact between the spherical outer surface of the section 1003 and the conical inside wall 1016a is tangential to the spherical outer surface of the section 1003. Hence, contact between the section 1003 and the wall 1016a occurs around an annulus defining a circular contact zone. This circular contact zone provides uniform compression of the chamber 1011 by the sleeve 1008 to ensure that the head 1004 of bone anchor 1005 is firmly clamped with the chamber 1011. The clamping power of the chamber can be increased by roughening or structuring the contact surface of the chamber 1011 and or the contact surface of the head 1004 of the bone anchor 1005.

Figure 24:
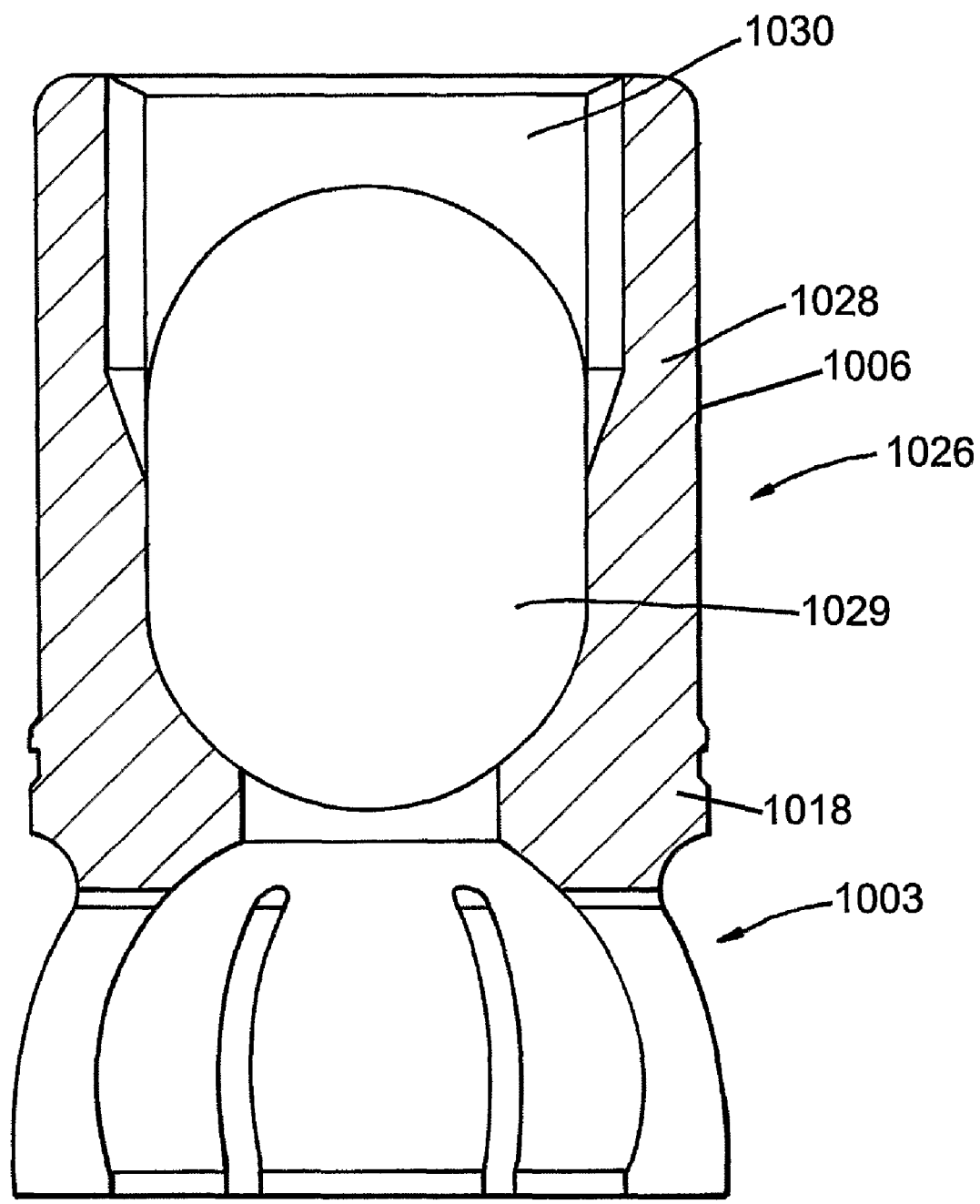
FIG. 24 is a longitudinal cross-section of a closed connector body.

In addition to the provision of top loading, in situ click-on, click off connectors 10 as shown in FIGS. 1 to 2 or side loading, in situ click-on, click-off connectors 1000 shown in FIGS. 19-23, the set may also comprise a variety of closed, in-situ click-on, click-off connectors 1026, an example of which is shown in FIG. 24. The structure of these connectors 1026 will now be described but it should be appreciated that it includes a first section 1003 for connection to a head 1004 of a bone anchor 1005 as described above. This section 1003 is identical to those of the connector 1000, in both construction and size and will not be described again.

With reference to FIG. 24, the embodiment of closed in situ click-on, click-off connector 1026 shown therein comprises the body portion 1002 with adjacent annular step portions 1018, as described above. Adjacent the step portions 1018, the connector 1026 comprises a substantially cylindrical body portion 1028 that is provided with a bore 1029 therethrough. The bore 1029 is provided to accommodate a support rod of circular cross-section but the bore 1029 preferably has a substantially oval profile to permit enough play for the support rod 1007, that connector 1026 can be threaded onto the support rod 1007 prior to the click-on of the connector 1026 to the bone anchor 1025. The feature of threading the connector 1026 on to the support rod 1007 prior to the click-on of the connector 1026 to a bone anchor, yields the benefit that support rod 1007 and connectors 1026 can be assembled into a construct outside of the patient. The construct can then be implanted and clicked onto the bone anchors and secured in a single step, thereby saving the practitioner valuable time during a surgical procedure. To prevent the support rod from slipping out of the connectors during the implantation, one or more stoppers can be installed on either side of the rod after the connectors 1026 have been threaded onto it.

The closed connector 1026 has no need for a member 1010. However, a locking fastener (not shown) can be screwed down into the body 1026 in a threaded aperture 1030 provided at the opposite end of the connector 1026 to the section 1003.

In some embodiments of the invention, locking the connector 1026 is a two-stage operation. Once the connector 1026 has been provisionally locked by movement of the sleeve 1008 partially over the section 1003, the locking cap is screwed down into the aperture 1030. In a similar fashion to the locking of the connector 1001, the cap bears down on the support rod 1007 inserted through the bore 1029 so that it pushes down on the sleeve 1008 forcing it further over the section 1003 of the connector 1026. As the cap is tightened, the support rod 1007 becomes clamped into the bore 1029 by the cap and the sleeve 1008 adopts a similar final position similar to that shown in FIGS. 21 to 23.

In a spinal fixation implant set, a plurality of connectors 10,1000,1026 and bone anchors 12,1005 are provided that can be used interchangeably with one another. To this end, a variety of top-loading, side-loading and closed, in situ click-on, click off connectors as described above may be supplied for use with a variety of differently sized support rods. FIGS. 21 to 23 show three different embodiments of connector 1000 which are all constructionally similar to one another but adapted to accommodate support rods 1007 with diameters of 6 mm, 5 mm and 3.5 mm respectively. It can be seen that the height of the section 1006 of the connector 1000 and therefore the height of the retaining member 1010 vary dependent on the size of the support rod but in all three cases, the dimensions of the section 1003 of connector 1000, the size of the chamber 1011 and the size of sleeve 1008 are all identical. It is contemplated that the rod sizes and types of connectors are not limited to those described herein.

Likewise, the bone anchor can take the form of a screw, such as a pedicle screw, or a hook and a range of different types of anchors of varying dimensions, materials and construction may be provided in the spinal fixation implant set in accordance with the invention. However, in all cases, the part spherical heads of the anchors may always be the same shape and size so that any of the connectors in the set can be clicked onto any anchor. If the anchor is a screw, then the head can be provided, in addition with a socket for engagement with a screwdriver to allow fixation of the screw into the patient's bone. Normally, the anchor will be secured to the patient before being clicked into the connector. However, the connector preferably is provided with an aperture such as the aperture 1013 to permit access to the head to allow adjustments to be made after the connector has been clicked onto the connector but before final locking has taken place.

Figure 25:
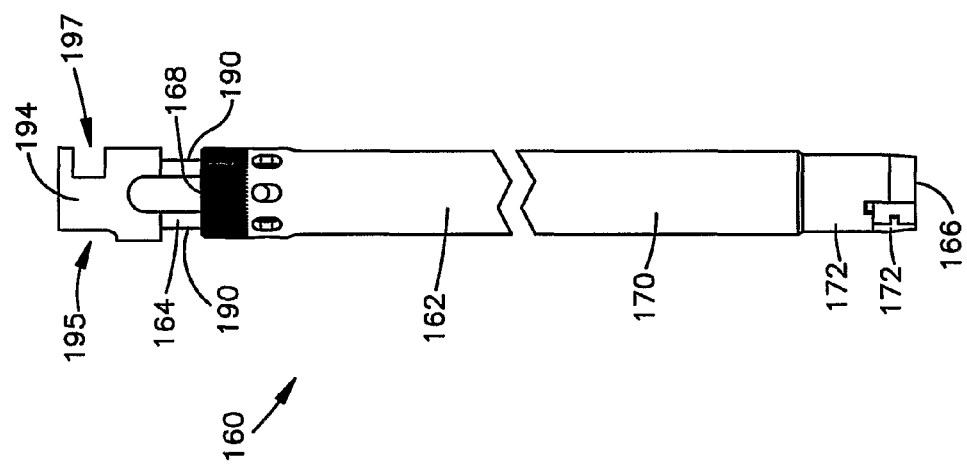
FIG. 25 is a side view of an implant holder for installing the bone fixation assembly shown in FIGS. 1 and 2.
Figure 27:
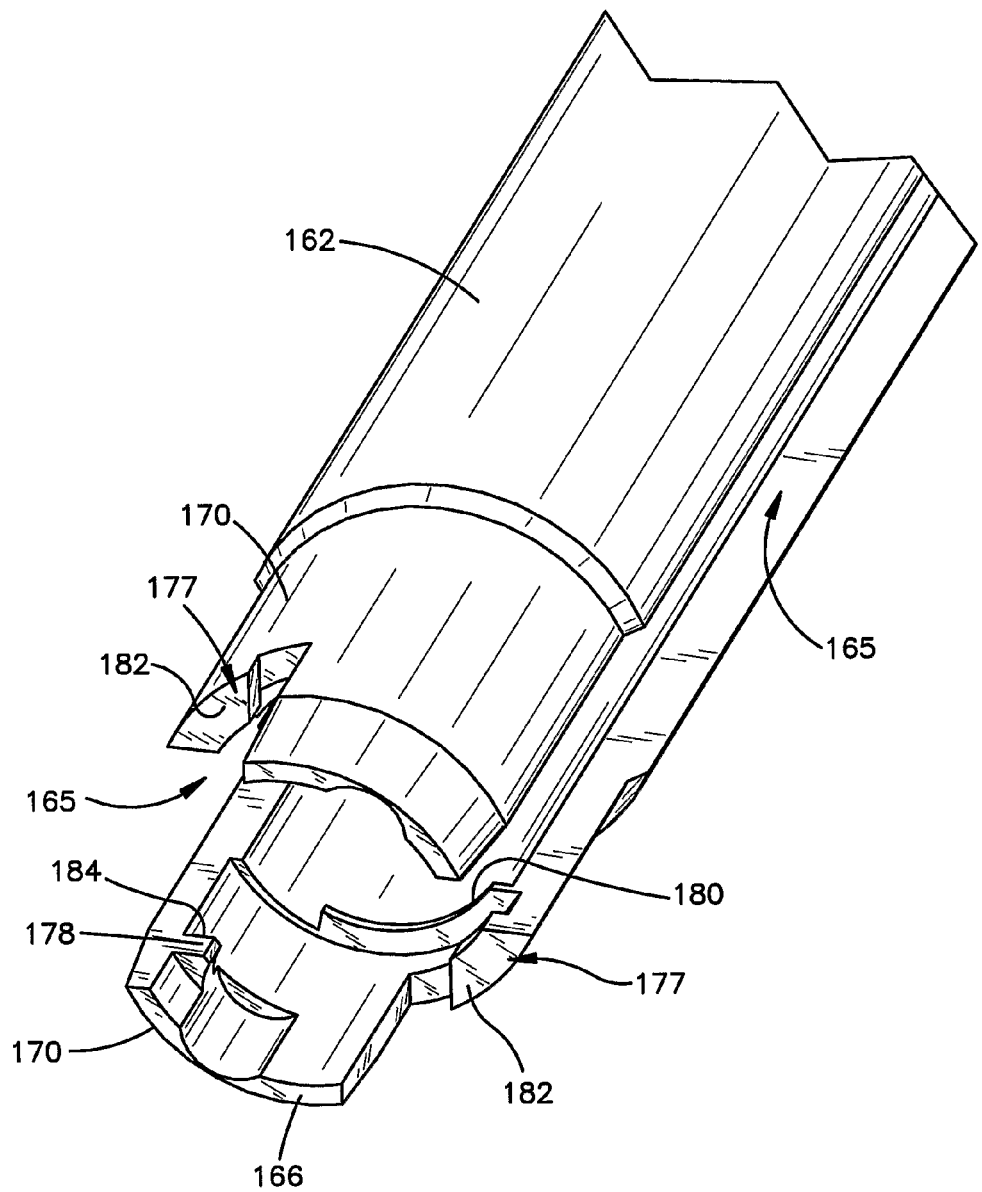
FIG. 27 is an enlarged, partial perspective view of the part shown in FIG. 26.

Tools are provided for installing the connector devices 10 on the pedicle screws 12. These include an implant holder 160, as shown in FIG. 25. The implant holder 160 is a generally cylindrical two-piece device including a guide tube 162 and an implant extender 164 within the guide tube 162. Although a single implant holder 160 is shown in the drawings preferably it is one of a number of identical implant holders that preferably correspond to the number of connector devices 10 on the pedicle screws 12.

Figure 26:
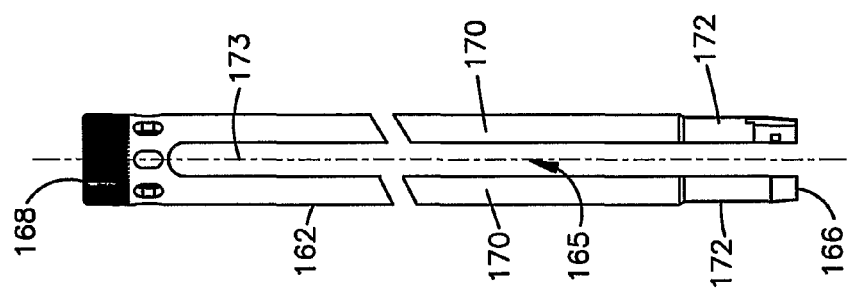
FIG. 26 is a side view of a part of the implant holder of FIG. 25.

As shown in the side view of FIG. 26, the guide tube 162 has a pair of diametrically opposed slots 165 extending axially upward from its lower end 166 nearly to its upper end 168. The slots 165 divide the tube 160 into segments 170. Lower end portions 172 of the segments 170 have configurations that are the same as each other, with one having an orientation rotated 180° from the other about the central axis 173 of the tube 162.

As shown in FIGS. 27-30, each lower end portion 170 of the guide tube 162 has a notch 177, a projection 178, and a flange 180. The length of the notch 177 extends upward from the lower end 166 of the tube 162. The width of the notch 177 begins at one of the slots 165 and extends partly around the tube 162. The notch 177 thus adjoins one of the slots 165 and is spaced laterally from the other slot 165. A short horizontal edge surface 182 extends partly across the upper end of the notch 177.

The projection 178 is located inside the tube 160 at a location spaced laterally from the notch 178. More specifically, the projection 178 extends radially inward at a location adjacent to the slot 165 that is spaced laterally from the notch 177. A surface 184 of the projection 178 faces axially upward within the tube 160. The flange 180 also is located inside the tube 160, and projects radially inward above the notch 177.

Figure 33:
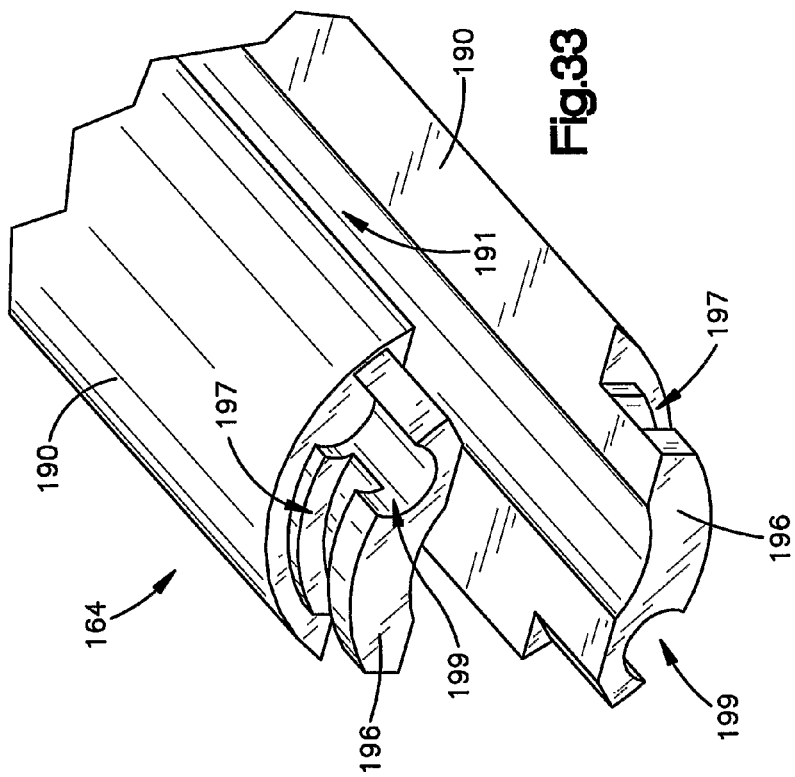
FIG. 33 is an enlarged, partial perspective view of the part shown in FIGS. 31 and 32.
Figure 32:
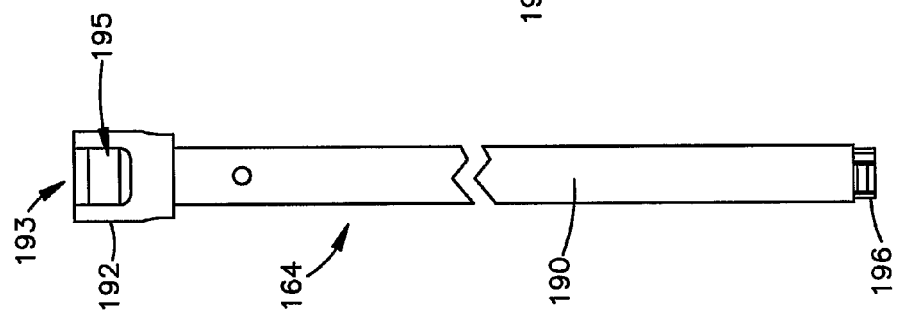
FIG. 32 is a view taken along line 32-32 of FIG. 31.
Figure 31:
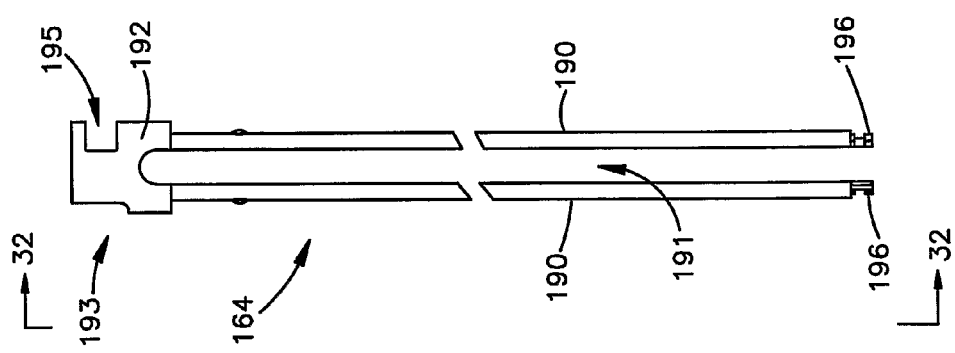
FIG. 31 is a side view of another part of the implant holder of FIG. 25.

The implant extender 164 (FIGS. 31-33) also is a vertically elongated tool with a pair of cylindrical segments 190 separated by diametrically opposed slots 191. A short generally cylindrical cap 192 at the upper end of the extender 164 has a notch 193 extending downward from the top at one side. A slot 195 extends partially across the cap 192 at the other side. Like the lower end portions 172 of the tube 162, the lower end portions 196 of the extender 164 are alike and are oriented opposite relative to each other. Each has a horizontally extending groove 197 preferably intersecting a vertically extending groove 199.

Figure 35:
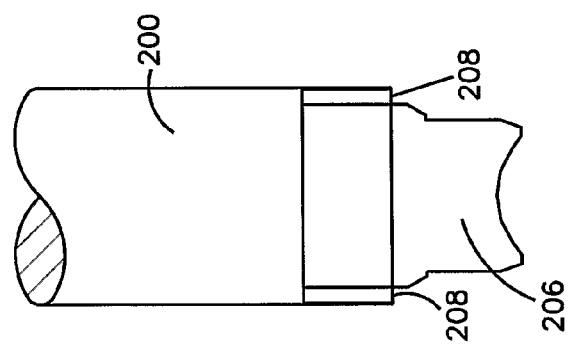
FIG. 35 is an enlarged partial view of the pusher shown in FIG. 34.
Figure 34:
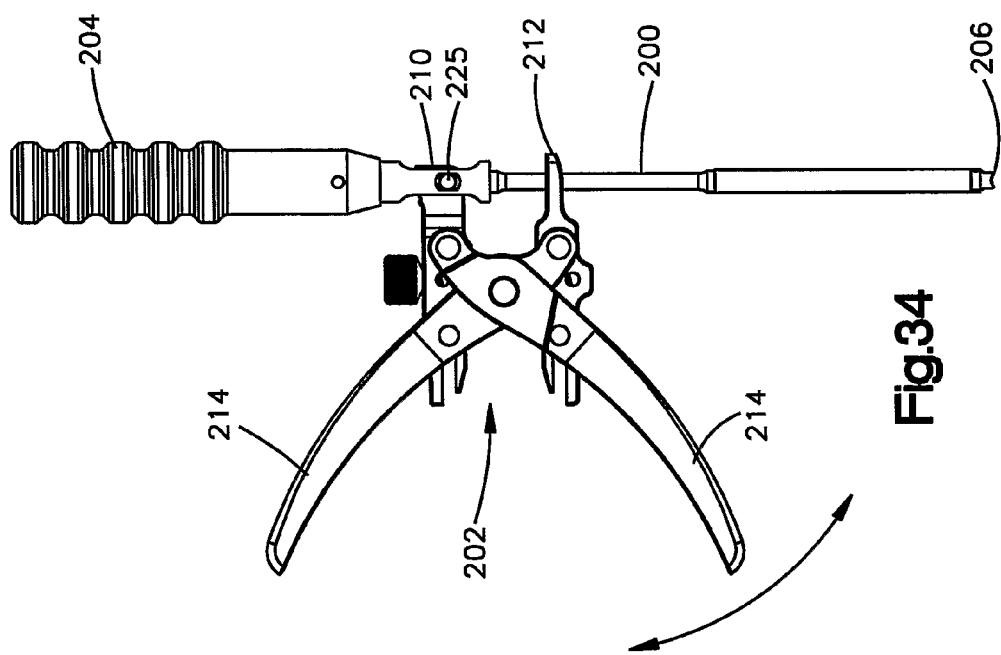
FIG. 34 is a side view of a pusher with an actuator for use with the implant holder of FIG. 25.

FIG. 34 shows a pusher 200 with an actuator 202. The pusher 200 is an elongated member with a hand grip 204 at its upper end and a pusher bar 206 at its lower end. As shown in FIG. 35, the pusher bar 206 has a pair of parallel shoulder surfaces 208. Upper and lower claws 210 and 212 on the actuator 202 move toward each other when the actuator handles 214 are squeezed together. The upper claw 210 is pivotally connected at pivot 225 to the pusher 200 so that the actuator 202 can swing into and out of the position of FIG. 34, as indicated by the arrow shown in the drawing.

Figure 36:
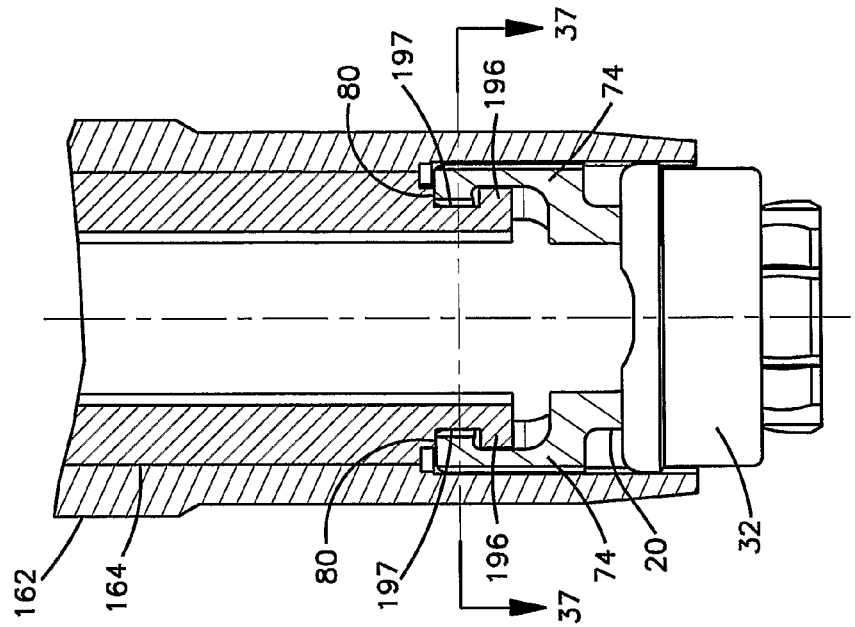
FIG. 36 is a sectional view showing parts in positions taken during the installation process.
Figure 37:
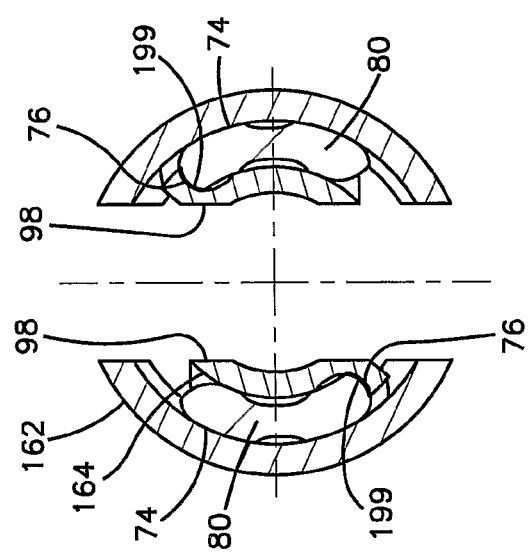
FIG. 37 is a sectional view taken along line 37-37 of FIG. 36.

Several steps are taken in the process of installing a connector device 10 with the tools 160, 200 and 202 to a bone anchor. The process begins with a connector body 20 that has a sleeve 32 in the temporary position (FIG. 11). In a preferred sequence of steps, implant holder 160 is first attached to the connector body 20. To do this, implant holder 160 preferably is first arranged as shown in FIG. 25 with the segments 190 of the extender 164 offset 90° from the segments 170 of the guide tube 162. The implant holder 160 is moved downward over the connector body 20 until the flanges 180 inside the guide tube 162 (FIGS. 27 and 30) move downward into abutment with the arms 74 on the body 20. The extender 164 is then rotated approximately 90° clockwise relative to the guide tube 162 and the body 20. This moves the slots 191 in the extender 164 into alignment with the slots 165 in the guide tube 162. This also moves the lower end portions 196 of the extender 164 across the arms 74 of the body 20 so that the rims 80 on the arms 74 are received in the horizontal grooves 197 (FIG. 33) on the extender 164, as shown in FIG. 36. The vertical grooves 199 on the extender 164 (FIG. 33) move against the adjacent side edges 76 of the arms 74 to stop the extender 164 from rotating beyond the position shown in FIG. 37. When the rims 80 are located within the grooves 197 in this manner, the extender 164 is axially interlocked with the body 20.

Figure 38:
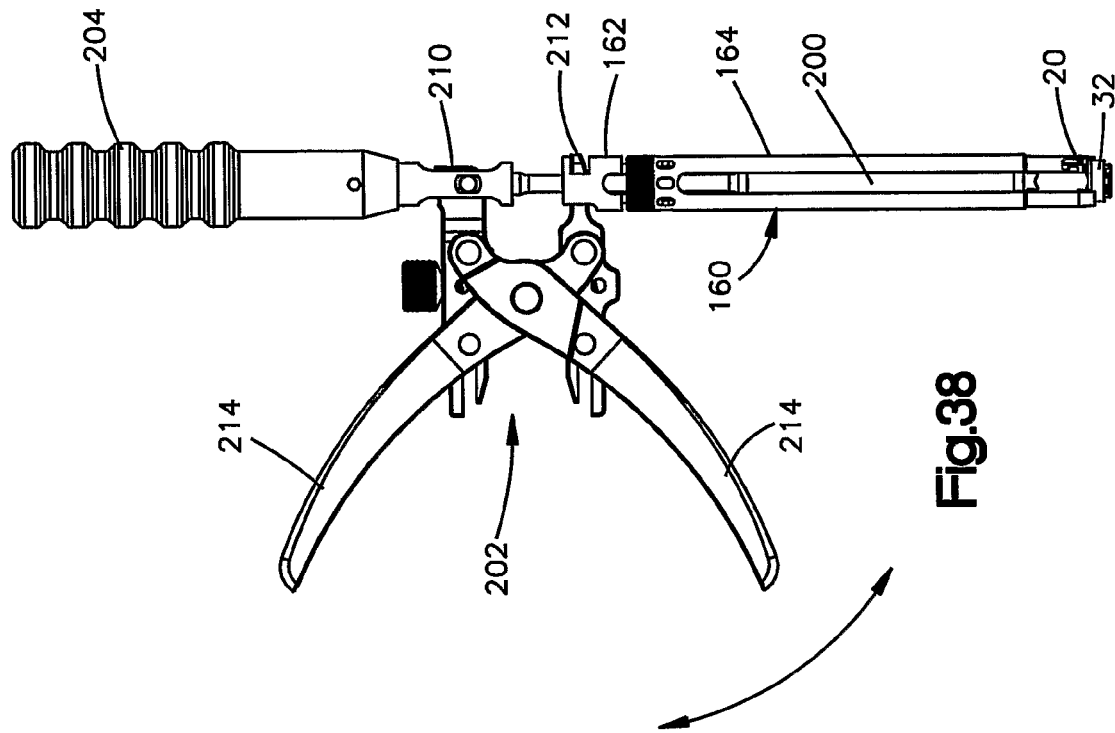
FIG. 38 is a full side view of parts shown in FIG. 36.

In the next step, the pusher 200 is inserted downward through the extender 164 and the surrounding guide tube 162, as shown in FIG. 38. The actuator 202 is moved pivotally so that the lower claw 212 is moved into and through the notch 193 and slot 195 in the cap 192 at the top of the extender 164. With the bone anchor preferably implanted in a vertebrae, the surgeon then presses the entire assembly of tools downward against the pedicle screw 12 to snap the bone anchor into the socket 47 of the connector body 20. The connector body 20 at this point is now connected to the bone anchor, but removable from the bone anchor because the sleeve 32 has not moved into the provisional locking position to prevent outward flexing of the segments 50.

The surgeon next squeezes the actuator handles 214. As the claws 210 and 212 move toward each other, the upper claw 210 drives the pusher 200 downward through the extender 164, as indicated by the arrow shown in FIG. 39. An axially upward reaction force is transmitted to the connector body 20 by the extender 164 because the extender 164 is axially interlocked with the body 20. This enables the pusher bar 206 to move forcefully against the sleeve 32 to snap the sleeve 32 downward from the temporary position to the provisional locking position (FIG. 12). Downward movement of the sleeve 32 is stopped when the shoulder surfaces 208 of the pusher bar 206 land on the shoulder surfaces 78 of the body 20.

Having placed the sleeve 32 in the provisional locking position in the foregoing manner, the surgeon withdraws the pusher 200 and the actuator 202 from the implant holder 160.

This is accomplished by pivoting the actuator 202 upward to move the lower claw 212 out of engagement with the extender 164 at the cap 194, and by lifting the actuator 202 and pusher 200 upward together. The implant holder 160 is left in place on the connector body 20. This portion of the process is repeated until connector bodies 20 with sleeves 32 and implant holders 160 are mounted on all of the pedicle screws 12. Other ways of connecting the connector body onto the bone anchor and moving the sleeve 32 to the provisional locking position are contemplated.

The provisional locking positions of the sleeves 32 permit the connector bodies 20 to angulate into alignment on the row of pedicle screws 12. Corresponding angulation of the implant holders 160 enables the spinal fixation rod 14 to be inserted longitudinally through the aligned slots 165 and 191 in the implant holders 160. The rod 14 is next moved downward along the slots 165/191 and into the channels 71 in the connector bodies 20.

An alternate pusher 220 with a wider pusher bar 222 (FIG. 40) may be used to press the rod 14 firmly downward to a location beside the notches 177 in each guide tube 162. The surgeon then rotates each guide tube 162 approximately 45° to move the notches 177 over the rod 14, as shown in FIG. 41. The edge surfaces 182 at the upper ends of the notches 177 block the rod 14 from moving back upward. The projections 178 inside the guide tube 162 simultaneously slide beneath the rim of the connector body 20 to block the guide tube 162 from moving upward. Rotating the guide tube 162 into the position of FIG. 35 in this manner temporarily interconnects the rod 14 with the guide tube 162 and the connector body 20 by clamping the rod 14 between the guide tube 162 and the connector body 20. This restrains the rod 14 from moving relative to the connector body 20 prior to installation of the locking cap 30. The surgeon then swings the actuator 202 sideways to rotate the extender 164 out of axially interlocked engagement with the arms 74 of the connector body 20, and lifts the actuator 202 to withdraw both the extender 164 and the pusher 220 from the guide tube 162. These steps are repeated at all of the implant holders 160 so that all of the guide tubes 162 (with the extender 164 removed) are temporarily interconnected with the rod 14 and the connector bodies 20 above the pedicle screws 12 in readiness to receive the locking caps 30.

Figure 45:
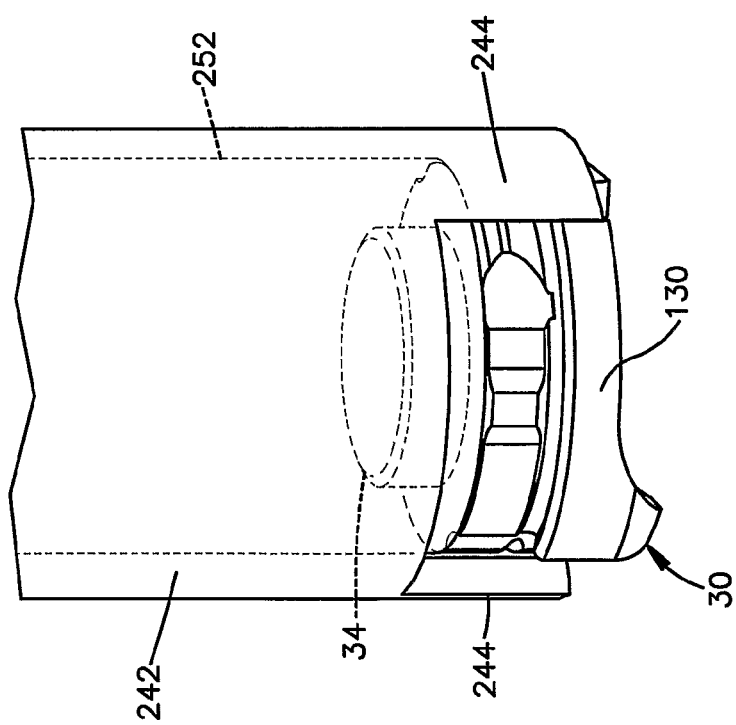

The tool 240 shown in FIGS. 42 and 43 is a counter-torque instrument with an insertion tube 242 that fits inside the guide tube 162. A pair of cylindrically contoured segments 244 are located at the bottom of the insertion tube 242. A handle 246 projects laterally from the top of the insertion tube 242. The tool 250 shown in FIG. 44 is a cap holder with a shaft 252 for reaching downward through the insertion tube 242. An internal screw thread 254 at the bottom of the shaft 252 matches the external screw thread on the set screw 34 at the top of the locking cap 30 (FIG. 1). The shaft 252 is placed downward through the insertion tube 242 before the shaft is screwed into attachment with the set screw 34. As shown in FIG. 45, the segments 244 of the insertion tube 242 fit closely between the flanges 130 on the cap 30 to block the cap 30 from rotating while the shaft 252 is being screwed onto the set screw 34. When the shaft 252 has been screwed onto the set screw 34 as shown in FIG. 45, the shaft 252 can be extended further downward through the insertion tube 242 to move the cap 30 out from between the segments 244 of the insertion tube 242, as shown in FIG. 46.

Figure 46:
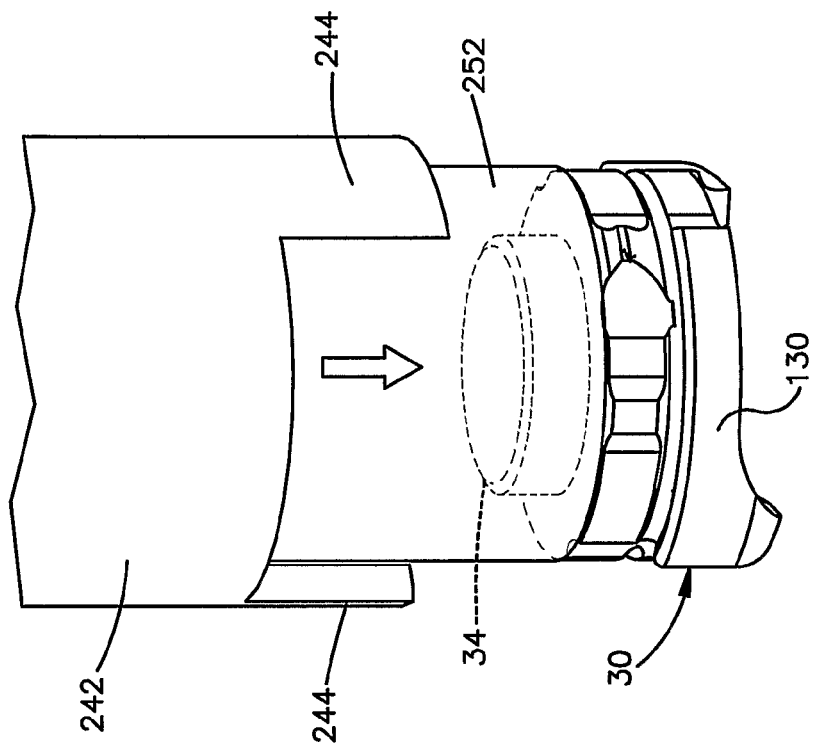
FIGS. 45 and 46 are perspective views showing the same parts in different positions taken during the installation process.

The interconnected parts shown in FIG. 46 are moved downward through the guide tube 162 to place the locking cap 30 on the connector body 20 in the partially installed position of FIG. 16. A hand grip 258 at the top of the cap holder 250 enables the surgeon to rotate the shaft 252, and thereby to rotate the attached cap 30 into the installed position of FIG. 18. After rotation of the locking cap, the insertion tube 242 is pushed down fitting the segments 244 in-between the flanges 130 on the cap 30 to prevent the cap 30 from rotating while loosening the shaft 252 counter-clockwise.

The next step may be to tighten the set screw 34 downward against the rod 14. A screwdriver (not shown) is inserted downward through the insertion tube 242 to tighten the set screw 34. The segments 244 of the insertion tube 242 are still positioned in-between the flanges 130 on the cap 30. The surgeon then holds the handle 246 firmly to transmit a counter-torque to the arms 74 while tightening the set screw 34. The counter-torque restrains the cap 30 from rotating under the influence of torque transmitted to the cap 30 as the set screw 34 is being tightened.

When the set screw 34 is being tightened downward against the rod 14, it presses the rod 14 downward against the upper end 91 (FIG. 2) of the sleeve 32. The rod 14 presses the sleeve 32 downward from the provisional locking position to the locking position in which the sleeve 32 prevents further angulation of the connector body 20 on the bone anchor 12. Tightening the set screw also clamps the spinal rod in the channel of the connector body to prevent movement of the spinal rod. As discussed earlier, the surgeon may lock angulation of the bone anchor relative to the connector body independently of locking the spinal rod relative to the connector body by moving the sleeve 32 down so that it compresses the lower section 40 of the connector body.

The counter-torque instrument 240 can also be used to prevent the cap 30 from being accidentally rotated backwards when loosening of the set screw 34 is required for parallel distraction or compression with locked screw head 22, respectively.

This written description sets forth the best mode of carrying out the invention, and describes the invention in a manner to enable a person of ordinary skill in the art to make and use the invention, by presenting examples of the structural elements recited in the claims. The patentable scope of the invention is defined by the claims, and may include other examples that occur to those skilled in the art. Such other examples, which may be available either before or after the application filing date, are intended to be within the scope of the claims.

The invention claimed is:

1. An apparatus for connecting a bone anchor to a support rod, comprising:
 a connector body having an upper portion, a middle portion, and a lower portion, the lower portion including a socket for polyaxially receiving a head portion of the bone anchor, the upper portion including a pair of diametrically opposed arms defining a rod-receiving channel for receiving the support rod, each arm including an inner surface, an outer surface, opposite edge surfaces, a rim projecting radially inward, and a recess formed in the rim; and
 a cap sized and configured to engage the inner surfaces of the arms, the cap including a pair of bosses projecting radially outward, a pair of stoppers projecting radially outward, and a pair of flanges projecting radially outward and located beneath the bosses and stoppers;
 wherein the cap is receivable in the channel in a partially installed position in which the bosses, stoppers and flanges are located circumferentially between the arms of the connector body, rotation of the cap from the partially installed position toward an installed position causes the arms to interfere with further movement of the bosses, and further rotation of the cap to the installed position causes 1) the arms to deflect outwardly to move out of interference with the bosses such that the bosses are movable past the rim on each arm so as to be received in the recesses, and 2) the stopper to abut a side edge of an arm.

2. The apparatus of claim 1, further comprising a sleeve receivable over at least a portion of the lower portion of the connector body, the sleeve being moveable between (i) a temporary position in which the sleeve permits insertion of the bone anchor, (ii) a provisional locking position in which the sleeve permits polyaxial angulation of the bone anchor with respect to the connector body but prevents removal of the bone anchor from the connector body, and (iii) a locking position in which the sleeve prevents both polyaxial angulation and removal of the bone anchor with respect to the connector body.

3. The apparatus of claim 2, wherein the sleeve includes a plurality of inwardly projecting retainer flanges receivable against the connector body in an interference fit from which the sleeve is releasable for movement toward the locking position.

4. The apparatus of claim 3, wherein the connector body has a substantially cylindrical outer surface with an upper step portion and a lower step portion, and the retainer flanges are deflectable to establish the interference fit upon moving axially onto the step portions of the cylindrical outer surface.

5. The apparatus of claim 4, wherein the middle section of the connector body comprises the substantially cylindrical outer surface, the connector body comprising a concave transition portion between the lower portion and the middle portion, the projecting retainer flanges receivable in the concave transition portion to prevent the sleeve from moving axially and for contacting the substantially cylindrical outer surface.

6. The apparatus of claim 2, wherein the sleeve is prevented from axial and rotational movement with respect to the connector body when in the temporary position.

7. The apparatus of claim 2, wherein the sleeve engages the connector body via an interference fit in the temporary position.

8. The apparatus of claim 2, wherein the sleeve is further configured to fit over the connector body in a preliminary position in which the sleeve is freely movable axially and rotationally relative to the connector body, and to move axially to the temporary position.

9. The apparatus of claim 2, wherein the connector body has a substantially cylindrical outer surface with one or more radially raised step portions, and the sleeve has one or more inner retainer portions that are moveable axially against the step portions of the cylindrical outer surface to establish an interference fit with the connector body upon movement of the sleeve axially from the preliminary position to the temporary position.

10. The apparatus of claim 2, wherein the sleeve is configured (i) to be received over the connector body in a first preliminary position upon movement of the sleeve axially over the connector body in a first direction, (ii) to be rotated from the first preliminary position to a second preliminary position, and (iii) to move from the second preliminary position to the temporary position, onward to the provisional locking position, and further to the locking position upon movement of the sleeve axially over the connector body in a second direction opposite the first direction.

11. The apparatus of claim 1, wherein when the cap is rotated from the partially installed position to the installed position, the bosses contact and deflect the arms radially outward to enlarge the channel so that the flanges formed on the cap can be circumferentially aligned with the rim formed on the arms.

12. The apparatus of claim 11, wherein when the cap is located in the installed position, the bosses are received in the recesses formed on the rim so that the arms will return to their original undeflected conditions causing the rim formed on the connector body to engage at least a portion of the flange formed on the cap.

13. The apparatus as claim 12, wherein the bosses project radially outward in diametrically opposed positions on the cap, the stoppers project radially outward in diametrically opposed positions on the cap, the stoppers are circumferentially offset about 45 degrees from the bosses, and the flanges extend about 90 degrees about the periphery of the cap.

14. The apparatus of claim 1, wherein the arms are configured to deflect radially outward under the influence of the bosses when the cap is rotated from the partially installed position to the installed position, and to snap back inward to capture the bosses in the recesses when the cap reaches the installed position.

15. The apparatus of claim 14, wherein the arms are located in the rotational path of movement of the flanges when the cap is in the partially installed position, and the bosses are configured to deflect the arms radially outward to provide clearance for the flanges to move beneath the rims as the cap is rotated into the installed position.

16. The apparatus of claim 1, wherein when the cap is rotated from the partially installed position to the installed position, the cap is rotated relative to the connector body but the cap does not move axially relative to the connector body.

17. The apparatus of claim 1, wherein the cap is axially movable into the partially installed position without rotating relative to the connector body.

18. The apparatus of claim 1, wherein when the cap is rotated from the partially installed position to the installed position, the flanges are configured to move circumferentially beneath the rims without camming action.

19. The apparatus of claim 1, wherein when the cap is rotated from the partially installed position to the installed position, the bosses formed on the cap are configured to snap into the recesses formed on the arms while the flanges formed on the cap are configured to move circumferentially beneath the rims formed on the arms.

20. The apparatus of claim 1, wherein when the cap is rotated from the partially installed position to the installed position, the stoppers move into abutment with the connector body to block continued rotation of the cap beyond the installed position.

21. The apparatus of claim 1, wherein the flanges are located beneath the rims.

22. An apparatus for connecting a bone anchor to a support rod, comprising:
  a connector body having an upper portion, a middle portion, and a lower portion, the lower portion including a socket for polyaxially receiving a head portion of the bone anchor, the upper portion including a shoulder surface and a pair of diametrically opposed arms defining a rod-receiving channel for receiving the support rod, each arm including an inner surface, an outer surface, opposite edge surfaces, a rim projecting radially inward, and a recess formed in the rim; and
  a cap including an upper portion and a lower portion and configured to engage the inner surfaces of the arms, the cap including a pair of bosses projecting radially outward, a pair of stoppers projecting radially outward, a pair of flanges projecting radially outward and located beneath the bosses and stoppers, and at least two projections extending from the lower portion of the cap;

wherein the cap is receivable in the channel in a partially installed position in which the bosses, stoppers and flanges are located circumferentially between the arms of the connector body, and wherein when the cap is rotated from the partially installed position to an installed position, the bosses are received in the recesses, the stopper abuts a side edge of an arm, the flanges are located beneath the rims, and the at least two projections contact the shoulder surface.

23. The apparatus of claim 22, wherein the flange extends radially from the lower portion of the cap, below both the bosses and stoppers which extend radially from the upper portion of the cap.

24. An apparatus for connecting a bone anchor to a support rod, comprising:

a connector body having an upper portion, a middle portion, and a lower portion, the lower portion including a socket for polyaxially receiving a head portion of the bone anchor, the upper portion including a pair of diametrically opposed arms defining a rod-receiving channel for receiving the support rod, each arm including an inner surface, an outer surface, opposite edge surfaces, a rim projecting radially inward, and a recess formed in the rim; and a cap including an upper portion and a lower portion and configured to engage the inner surfaces of the arms, the cap including a pair of bosses projecting radially outward, a pair of stoppers projecting radially outward, and a pair of flanges projecting radially outward;

wherein the cap is receivable in the channel in a partially installed position in which the bosses, stoppers and flanges are located circumferentially between the arms of the connector body, the cap is rotatable from the partially installed position toward an installed position such that the arms interfere with movement of the bosses, and the cap is further rotatable to the installed position such that the arms deflect outwardly to permit the bosses to move past the rim on each arm and the bosses are received in the recesses, the stopper abuts a side edge of an arm, and the flanges are located beneath the rims;

wherein the flanges guide the rotation of the cap within the arms to the installed position such that the bosses deflect the arms outwardly to move out of interference with the bosses, the bosses snap into the recesses when the cap is in the installed position, and the engagement of the stopper with the side edge of the arm prevents over-rotation of the cap.

25. The apparatus of claim 24, wherein the flanges each further comprise a rounded contour following along the entire perimeter of each flange, wherein the rounded contours complement the underside of the rim of the connector body.

26. The apparatus of claim 24, wherein the flanges extend continuously along at least 90 degrees of the circumference of the cap and located beneath the bosses and stoppers.

* * * * *